United States Patent [19]

Taniguchi et al.

[11] Patent Number: 5,399,669
[45] Date of Patent: Mar. 21, 1995

[54] INTERLEUKIN-2 POLYPEPTIDES

[75] Inventors: Tadatsugu Taniguchi, Tokyo; Masami Muramatsu, Tokorozawa; Haruo Sugano, Tokyo; Hiroshi Matsui; Nobukazu Kashima, Tunji Hamuro all of Yokohama, all of Japan

[73] Assignees: Ajinomoto Co., Inc.; Japanese Foundation For Cancer Research, both of Tokyo, Japan

[21] Appl. No.: 96,842

[22] Filed: Jul. 26, 1993

Related U.S. Application Data

[63] Continuation of Ser. No. 631,228, Dec. 21, 1990, abandoned, which is a continuation of Ser. No. 356,653, May 17, 1989, abandoned, which is a continuation of Ser. No. 33,792, Apr. 3, 1987, abandoned, which is a continuation of Ser. No. 463,496, Feb. 3, 1983, Pat. No. 4,738,927.

[30] Foreign Application Priority Data

| Mar. 31, 1982 | [JP] | Japan | 57-51122 |
| May 18, 1982 | [JP] | Japan | 57-82509 |
| Dec. 15, 1982 | [JP] | Japan | 57-219518 |
| Dec. 24, 1982 | [JP] | Japan | 57-229619 |
| Dec. 27, 1982 | [JP] | Japan | 57-234607 |
| Dec. 29, 1982 | [JP] | Japan | 57-230371 |

[51] Int. Cl.⁶ .................................... C07K 13/00
[52] U.S. Cl. .................. 530/351; 435/69.52; 930/141; 424/85.2
[58] Field of Search .................... 530/351; 435/69.52; 930/141

[56] References Cited

U.S. PATENT DOCUMENTS

| 4,490,289 | 12/1984 | Stern | 530/351 |
| 4,564,593 | 1/1986 | Isukamoto et al. | 435/68 |
| 4,568,640 | 2/1986 | Robin | 435/68 |
| 4,778,879 | 10/1988 | Merulsmon et al. | 530/351 |
| 4,789,658 | 12/1988 | Yoshimoto et al. | 530/351 |

OTHER PUBLICATIONS

Henriksen et al. *Cell. Immunol*, 1982, pp. 106–114, vol. 73.
Walte et al, *J. Exp Med* 156, 1982, pp. 454–464.
Mechizuki et al, *J Immunol Methods* 39, 1980, pp. 185–201.
Staller et al, *J. Immuol*, 128 (4) 1982, pp. 1620–1624.

*Primary Examiner*—Garnette D. Draper
*Assistant Examiner*—Lorraine M. Spector
*Attorney, Agent, or Firm*—Oblon, Spivak, McClelland, Maier & Neustadt

[57] ABSTRACT

Recombinantly produced interleukin-2 exhibits human IL-2 activity, has a molecular weight of about 15,000 daltons, is activity stable at a pH of 2–9 and is resistant to elevated temperatures. The recombinant IL-2 has the principal biological activity of human IL-2, promotion of proliferation of cytotoxic T lymphocytes.

3 Claims, 15 Drawing Sheets

FIG.2(A)-1

```
ATCACTCTCTTAATCACTACTCACAGTAACCTCAACTCCTGCCACA
                                                1
                                                Met Tyr Arg Met GlN Leu Leu Ser Cys Ile Ala
                                                ATG TAC AGG ATG CAA CTC CTG TCT TGC ATT GCA
                                                 50
        20
Leu Ser Leu Ala Leu Val Thr AsN Ser Ala Pro Thr Ser Ser Thr Lys Lys Thr GlN Leu GlN Leu
CTA AGT CTT GCA CTT GTC ACA AAC AGT GCA CCT ACT TCA AGT TCT ACA AAG AAA ACA CAG CAA CTG
                    100
                            40
Glu His Leu Leu Asp Leu GlN Met Ile Leu AsN Gly Ile AsN AsN Tyr Lys AsN Pro Lys Leu Thr
GAG CAT TTA CTG GAT TTA CAG ATG ATT TTG AAT GGA ATT AAT AAT TAC AAG AAT CCC AAA CTC ACC
150                                                             200
         60                                                                          80
Arg Met Leu Thr Phe Lys Phe Tyr Met Pro Lys Lys Ala Thr Glu Leu Lys His Leu GlN Cys Leu Glu
AGG ATG CTC ACA TTT AAG TTT TAC ATG CCC AAG AAG GCC ACA GAA CTG AAA CAT CTT CAG TGT CTA GAA
                                         250
                                                                100                   353
Glu Glu Leu Lys Pro Leu Glu Glu Val Leu AsN Leu Ala GlN Ser Lys AsN Phe His Leu Arg Pro Arg
GAA GAA CTC AAA CCT CTG GAG GAG GTG CTA AAT TTA GCT CAA AGC AAA AAC TTT CAC TTA AGA CCC AGG
                 300
                                                     120
Asp Leu Ile Ser AsN Ile AsN Val Ile Val Leu Glu Leu Lys Gly Ser Glu Thr Thr Phe Met Cys Glu
GAC TTA ATC AGC AAT ATC AAC GTA ATA GTT CTG GAA CTA AAG GGA TCT GAA ACA ACA TTC ATG TGT GAA
                                                     400
```

```
                                                                              140
Tyr Ala Asp Glu Thr Ala Thr Ile Val Glu Phe Leu Asn Arg Trp Ile Thr Phe Cys Gln Ser Ile Ile
TAT GCT GAT GAG ACA GCA ACC ATT GTA GAA TTT CTG AAC AGA TGG ATT ACC TTT TGT CAA AGC ATC ATC
                                         450

153
Ser Thr Leu Thr
TCA ACA CTA ACT TGA TAATTAAGTGCTTCCCACTTAAAACATATCAGGCCTTCTATTTATTTAAATATTTAAATTTTATATTTATT
        500                                              550

GTTGAATGTATGGTTTGCTACCTATTGTAACTATTATTCTTAATCTTAAAACTATATAAATATGGATCTCTTTATGATTCTTTTTGTAAGCCCT
                600                                              650

AGGGGCTCTAAAATGGTTTCACTTATTATTATCCCAAAATATTTATTATTATTATGTTGAATGTTAAATATAGTATCTATGTAGATTGGTTAGTAA
                        700                                              750

AACTATTT AATAAA TTTGATAAATATAAAAAAAAAAAAAAAC - poly(A)
                                 800
```

Amino Acid Sequence I

Met Tyr Arg Met Gln Leu Leu Ser Cys Ile Ala Leu Ser Leu Ala Leu Val Thr Asn
Ser Ala Pro Thr Ser Ser Thr Lys Lys Thr Gln Leu Gln Leu Glu His Leu Leu
Leu Asp Leu Gln Met Ile Leu Asn Gly Ile Asn Asn Tyr Lys Asn Pro Lys Leu Thr
Arg Met Leu Thr Phe Lys Phe Tyr Met Pro Lys Lys Ala Thr Glu Leu Lys His Leu
Gln Cys Leu Glu Glu Glu Leu Lys Pro Leu Glu Glu Val Leu Asn Leu Ala Gln Ser
Lys Asn Phe His Leu Arg Pro Arg Asp Leu Ile Ser Asn Ile Asn Val Ile Val Leu
Glu Leu Lys Gly Ser Glu Thr Thr Phe Met Cys Glu Thr Ala Asp Glu Thr Ala Thr
Ile Val Glu Phe Leu Asn Arg Trp Ile Thr Phe Cys Gln Ser Ile Ile Ser Thr Leu
Thr

Amino Acid Sequence II

Ala Pro Thr Ser Ser Thr Lys Lys Thr Gln Leu Gln Leu Glu His Leu Leu Leu
Asp Leu Gln Met Ile Leu Asn Gly Ile Asn Asn Tyr Lys Asn Pro Lys Leu Thr Arg

Met Leu Thr Phe Lys Phe Tyr Met Pro Lys Lys Ala Thr Glu Leu Lys His Leu Gln
Cys Leu Glu Glu Leu Lys Pro Leu Glu Glu Val Leu Asn Leu Ala Gln Ser Lys
AsN Phe His Leu Arg Pro Arg Asp Leu Ile Ser AsN Ile AsN Val Ile Val Leu Glu
Leu Lys Gly Ser Glu Thr Thr Phe Met Cys Glu Tyr Ala Asp Glu Thr Ile Val Glu
Phe Leu AsN Arg Trp Ile Thr Phe Cys GlN Ser Ile Ile Ser Thr Leu Thr

Amino Acid Sequence III

Pro Thr Ser Ser Ser Thr Lys Lys Thr GlN Leu GlN Leu Glu His Leu Leu Leu Asp
Leu GlN Met Ile Leu AsN Gly Ile AsN AsN Tyr Lys AsN Pro Lys Leu Thr Arg Met
Leu Thr Phe Lys Phe Tyr Met Pro Lys Lys Ala Thr Glu Leu Lys His Leu GlN Cys
Leu Glu Glu Glu Leu Lys Pro Leu Glu Glu Val Leu AsN Leu Ala GlN Ser Lys AsN
Phe His Leu Arg Pro Arg Asp Leu Ile Ser AsN Ile AsN Val Ile Val Leu Glu Leu
Lys Gly Ser Glu Thr Thr Phe Met Cys Glu Tyr Ala Asp Glu Thr Ala Thr Ile Val
Glu Phe Leu AsN Arg Trp Ile Thr Phe Cys GlN Ser Ile Ile Ser Thr Leu Thr

FIG. 2(B)-2

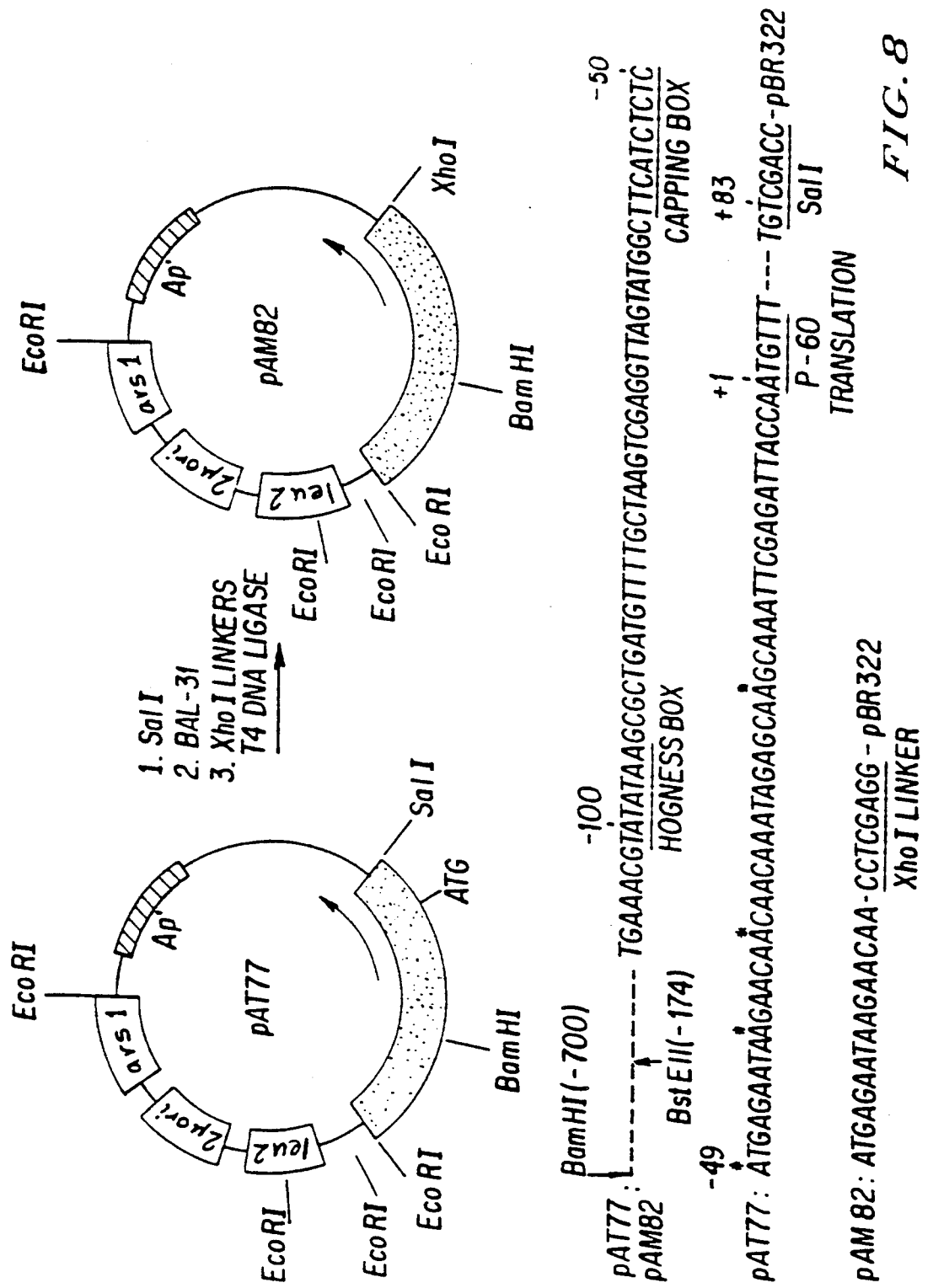

INTERLEUKIN-2 POLYPEPTIDES

This application is a continuation of application Ser. No. 07/631,228, filed Dec. 21, 1990, now abandoned, which was a continuation of application Ser. No. 07/356,653, filed May 17, 1989, abandoned, which was a continuation of application Ser. No. 07/033,792, filed Apr. 3, 1987, now abandoned, which was a continuation of application Ser. No. 06/463,496, filed Feb. 3, 1983, now U.S. Pat. No. 4,738,927.

BACKGROUND OF THE INVENTION

1. Field of the Invention

The present invention relates to agene, especially a cloned gene coding for a interleukin-2polypeptide, recombinant DNA carrying the gene, a living cell line possessing the recombinant DNA and a method for producing interleukin-2 using the cell line.

2. Brief Description of the Prior Art

Interleukin 2 (hereinafter referred to as "IL-2"), formerly referred to as T cell growth factor, is a soluble protein (generally known as "lymphokine"), and is produced froin T cells activated with a lectin or an antigen (Morgan. D. A., et al., Science, 193, 1007–1008 (1976), Gillis, S. et al., J. Immunol., 120, 2027–2033 (1978). Interleukin 2 (IL-2) is capable of modulating lymphocyte reactivity and promoting the in vitro long-term culture of antigen specific effector T-lymphocytes (Gillis. S. et al., Nature 268, 154–156 (1977)). IL-2 is also known to manifest other relevant biological activities such as enhancement of thymocyte mitogenesis (Chen, B. M. et al., Cell. Immunol., 22, 211–224, (1977), Shaw, J. et al., J. Immunol. 120, 1967–1973, (1978)), induction of cytotoxic T cell reactivity (Wagner, H. et al., Nature, 284, 278–280, (1980)) and anti-SRBC plaque forming cell responses (Gillis, S. et al., J. Exp. Med., 149, 1960–1968, (1979)) in cultures of nude mouse spleen cells. Accordingly, this lymphocyte regulatory substance is useful in potentiating humoral and cellular immune responses and in restoring immune deficient state to a normal humoral and cellular immune state. These identified immunological activities of IL-2 strongly indicate that IL-2 is useful for medical immunotherapy against immunological disorders including neoplastic diseases, bacterial or viral infections, immune deficient diseases, autoimmune diseases etc.(Papermaster, B. et al., Adv. Immunopharm., 507, (1980)). Like inteferons, IL-2 has been shown to augment natural killer cell activity, suggesting a potential use in the treatment of neoplastic diseases. Furthermore, IL-2 enables the maintenance of cultures of functional monoclonal T cells and hence appears to play a key role in the studying of the molecular nature of T cell differentiation, and of the mechanism of differentiated T cell functions as well as the mechanism of T cell antigen receptors. It is also useful for producing, by long term culturing of monoclonal T cell, many other T cell derived lymphokines, which are useful in a wide range of fields. In addition, IL-2 production and the response of lymphocytes to IL-2 can be important parameters of immunological functions which are useful in the clinical diagnosis of aberrant immunity.

IL-2 has been produced in the prior art by stimulating mouse, rat or human lymphocytes with a mitogen (Gillis. S. et al., Nature, 268, 154–156, 1977, Farrar, J. et al., J. Immunol., 121, 1353–1360,(1978). Gillis, S. et al., J. Immunol., 120, 2027–2033, 1978,)). By stimulating human peripheral blood mononuclear lymphocytes with a mitogen (Gillis. S. et al., J. Immunol., 124, 1954–1962, (1980)). Gillis et al. reported the preparation of murine IL-2 from murine T cell lymphoma cell line (Gillis. S. et al, J. Immunol., 125, 2570–2578 (1980)) and the preparation of human IL-2 from a human leukemia cell line (Gillis, S. et al., J. Exp. Med., 152, 1709–1719, (1980)).

The above noted articles by Gillis et. al. discuss the method of producing human IL-2 from mitogen-stimulated human T cell leukemia cell line by cell culture methods. However, such a technique results in undesirably low concentrations of human IL-2, and necessiates complex purification procedures to obtain even small amounts of IL-2 from a huge volumes of culture media. Moreover, since the human T cell leukemia cell lines produce trace amounts of many other biologically active substances which are analogous to human IL-2, significant difficulties are encountered in isolating IL-2 from these other immunologically active molecules, or in isolating IL-2 from the occasionally present toxic lectins.

As an alternative approach it would seem to be desirable to use recombinant DNA (DNA is an abbreviation for deoxyribo-nucleic acid) techniques as are used in the production of other biologically active human proteins, such as interferons, (Gray, P. W. et al., Nature, 295, 503–508, (1981), Nagata, S., et. al., Nature, 284, 316–320, (1980), Taniguchi, T. et. al., Gene, 10, 11–15, (1980)) to produce IL-2. However to date, attempts at the production of IL-2, by recombinant DNA techniques have not been successful. For instance, it was reported in "NIKKEI BIOTECHNOLOGY (Japan), No. 19, Jul. 5, 1982 that attempts to construct IL-2-producing organisms by recombinant DNAwere unsuccessful, probably due to the fact that the gene coding for IL-2 polypeptide had not yet been cloned.

A need therefore, continues to exist for a cloned gene, coded for interleukin-2, and for DNA produced recombinantly which carries the gene. A need also continues to exist for a living cell line which possesses the recombinantly produced DNA, and for a method of producing interleukin-2 using the cell line.

SUMMARY OF THE INVENTION

These and other objects of the present invention which will hereinafter become more readily apparent from the following description have been attained by providing:

A cloned gene coded for a polypeptide which possesses the activity of IL-2, and by providing:

A DNA, produced recombinantly which comprises a gene coded for a polypeptide possesses the activity of IL-2, and a vector DNA capable of replicating in a procaryotic or eucaryotic cell, the coding sequence of the said gene being located at a position downstream of a promoter sequence.

Further in accordance with the present invention, procaryotic or eucaryotic cell lines are provided which have been transformed to produce IL-2 with the above said DNA, vector DNA and coded gene. DNA capable of replicating in the cell; the coding sequence of said the gene being located at a position downstream of a promoter sequence.

In accordance with the present invention, IL-2 is produced by aerobically culturing a medium containing a eucaryotic or procaryotic cell line which has been transformed to produce IL-2 with a DNA which has been recombinantly modified by invention of a gene coded to produce which possesses the activity of IL-2, and, by insertion of a vector DNA, which is capable of replicating in the cell; the coding sequence of said gene being located at a position downstream of a promoter sequence.

BRIEF DESCRIPTION OF THE DRAWINGS

A more complete appreciation of the invention and many of the attendant advantages thereof will be readily attained as the same becomes better understood by reference to the following detailed description when considered in connection with the accompanying drawings, wherein:

FIG. 2(a) shows the base sequence of the cloned gene. FIG. 2(b) shows Amino Acid Sequence I, and Amino Acid Sequences II and III, of the polypeptides which possess IL-2 activity.

FIG. 8 is vector DNAs which are capable of replicating in a cell of *Saccharomyces cereviceae*

Figure 1:
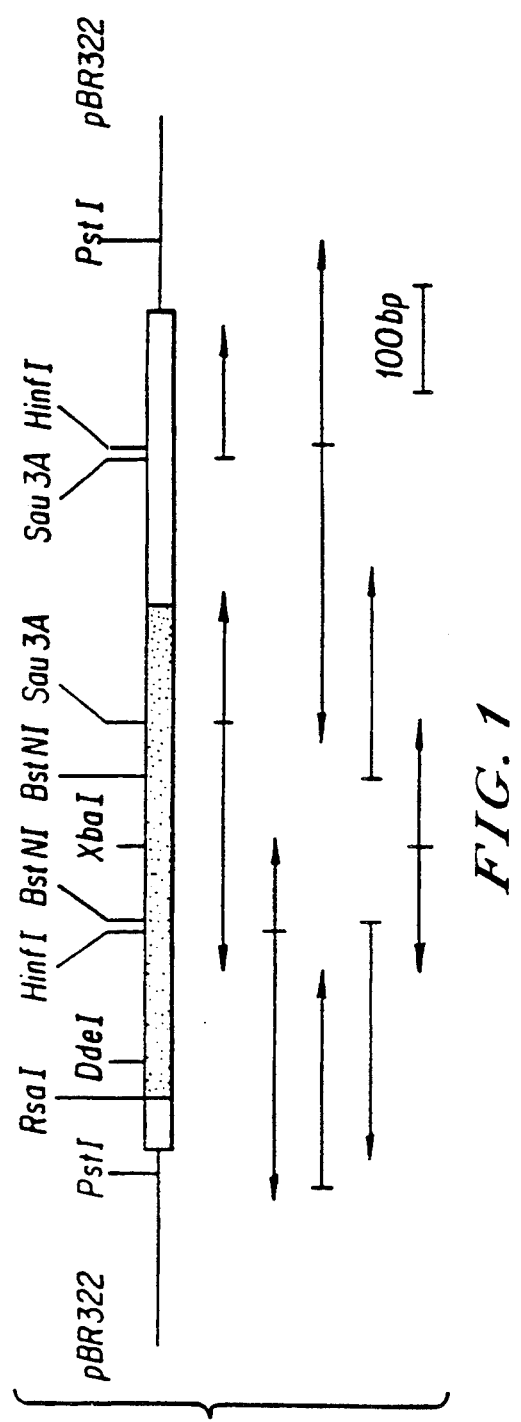
FIG. 1 shows a restriction endonuclease cleavage map of a cloned gene coded to produce a polypeptide which possesses the activity of IL-2 (hereinafter referred to as "IL-2 polypeptide").

In the Figures, "A", "G", "C" and "T" represent deoxyadenylic acid, deoxyguanylic acid, deoxycytidylic acid and thymidylic acid, respectively.

BRIEF DESCRIPTION OF THE PREFERRED EMBODIMENT

The cloned gene, coded for an IL-2 polypeptide, may be obtained by transcription of messenger RNA (mRNA; "RNA" is an abbreviation for ribonucleic acid) corresponding to IL-2 (hereinafter referred to as "IL-2 mRNA"), originating from a mammalian cell which is characterized by the capability of producing a polypeptide which possesses IL-2 activity, to a complementary DNA (cDNA). The single stranded cDNA (ss-cDNA) obtained can be converted into a double stranded cDNA (ds-cDNA).

The mRNA used as a template for the preparation of cDNA can be conventionally separated from a mammalian cell capable of producing IL-2 polypeptide. The separated RNA is polyadenylated (Gillis. et al., Immunological Rew., 63, 167–209 (1982)), and the polyadenylated RNA can be fractionated by, for example, centrifugation on a sucrose density gradient as a sediment of 11 to 12 S. Occasionally mRNA of 13 S will demonstrate IL-2 mRNA activity, and in those instances, it is presumed that the mRNA is in an aggregated form of 11 to 12 S mRNA.

The mammalian cells capable of producing IL-2 which are the source of mRNA of the present invention, may be T-lymphocytes, such as peripheral blood mononuclear cells, tonsil cells, spleen cells or the like, which are operationally obtainable from mammals. The cells may be conventionally pretreated such as with a nylon column, antiserum-complement, density gradient fractionation, multiple enzyme treatment such as a combination of neuraminidase and galactose oxidase, by x-ray irradiation or with trypsin to confer the cells with the IL-2 productivity or to increase the IL-2 activity. Also cloned T lymphocytes, obtained from the said mammalian cells after cultivation in the presence of T cell growth factor, may be also used as a source of mRNA and is the preferred T-lymphocytes. Transformed lymphocyte cell lines such as T lymphocytes derived from leukemia or lymphoma cell line per se or from their derivatives obtained by pretreatment or mutation by the methods mentioned above, or the cloned transformed cell lines are preferred as sources of the mRNA. Evidently, cloned cells line usually contain larger amounts of IL-2 mRNA as compared to parental bulk cell lines. T cell hybridomas, obtained by fusion of the lymphocyte derived cells mentioned above and tumor cell lines, such as CEM, Molt 4 F, and BW5147, are also preferred mammalian cell lines for use in this invention. In such instance the lymphocyte derived cell lines include (1) constitutive producers of IL-2 and (2) those which are producers of IL-2 only in the presence of a mitogen introduced into the culture, either in the absence or presence of other IL-2 production costimulatory cells.

In order to generate IL-2 mRNA in constitutive IL-2 producer cells, the constitutive IL-2 producer cells are cultured under conditions commonly known in the field of cell culture. For the generation of the mRNA in cells producing IL-2 only in the presence of mitogen, cultured cells are washed extensively with culture medium and resuspended in a culture medium, such as Rosewell Park Memorial Institute 1640 (hereinafter "RPMI 1640"), Dulbecco Modified Eagle Medium (hereinafter "DMEM") or in Click's medium, which may or may not contain serum. These culture media may be supplemented with various additives, such as penicillin, streptomycin or other antibiotics, or with fresh L-glutamine, Hepes buffer and sodium bicarbonate in a concentrations as are generally used in the field of cell culture. The preferred cell density may be from 0.5 to $4 \times 10^6$ cells/mi. To induce activation of the mRNA and production of IL-2, appropriate stimulants are added. Suitable such stimulants include mitogens, neuraminidase, galactose oxidase, zinc derivatives such as zinc chloride, or lymphocyte activating substances originated from microorganisms, such as protein A, streptolysin-O. The stimulated cells are recovered and washed. The co-presence of macrophages or dendritic cells during the mitogen stimulation may also activate the mRNA, or may increase the amount of the activated mRNA. Likewise the co-presence of cell lines derived from B lymphocytes or B lymphocyte lines, such as Raji, Daudi, K562, and BALL-1 may activate the mRNA or increase the amount of activated mRNA.

To propagate the mammalian cells, they are maintained in an in vitro cell culture or in histocompatibility matched animals, under normal conditions. When in vitro culture maintenance is used to prepare the source of mRNA, the cells may be grown in any of the culturing media as were previously found to foster growth of T cells. These culture media may or may not be supplemented with mammal serum, serum component or serum albumin. The culture period for the activation of the mRNA will correspond to the period necessary for the activation of cells to generate the mRNA. This period usually coincides with the time needed to start the excretion of IL-2 into the culture medium. The preferred period may be from 3 to 12 hours after. addition of a stimulant, such as a mitogen. Undue prolongation of the culture period may occasionally result in the decomposition of the generated IL-2 mRNA. During the course of the activation of IL-2 producing cells, phorbol esters, such as PMA or TPA may preferably utilized in a concentration from 10 to 50 ng/ml to boost the level of activation.

The above described process for activation of IL-2 mRNA may be carried out at temperatures ranging from 32° to 38° C. in a humidified atmosphere and in a pH of approximately 7.0 to 7.4.

The procedures to obtain and culture mammalian cells capable of producing IL-2 will now be explained.

(1) Acquisition of constitutively IL-2 producing cell line.

Jurkat cell line of human leukemic T cell (freely available from Fred Hutchinson Cancer Institue, Seattle, United States, Salk Institute, San Diego, United States, German Cancer Center, Heidelberg, West Germany) is suspended in Click's medium at a cell density of $1 \times 10^6$ cells/ml and $8 \times 10^3$ R x-ray is irradiated at irradiation rate of 150 R/min. Thereafter 0.1 cells of the thus irradiated cells per 200 μl of medium are inoculated into Click's medium containing 5% FCS in 96 well flat-bottom microplates (Falcon 3072) and cultured for 3 weeks at 37° C. in 5% $CO_2$ incubator (cloning by limiting dilution method). The grown viable cells are transferred into 24 well culture plate (Nunc) before the cell layer become confluent and is further cultured for 5 days. The grown cells are further cultured in serum and serum albumin free synthetic culture medium for about two days at a initial cell density of between $1-2 \times 10^6$/ml. The culture supernatant is harvested by centrifugation and filtered with 0.22 millipore filter paper to clear off debris and to sterilize the supernatant, and then x-ray treated mutants capable of producing IL-2 constitutively are selected and cloned by measuring the IL-2 activity present in the supernatant.

(2) Acquisition of IL-2 producer cell from human peripheral blood mononuclear cells.

Human peripheral blood is harvested and peripheral blood lymphocytes (hereinafter "PBL") are isolated by density gradient centrifugation on Ficoll-Hypaque. The PBL is inoculated in 2 ml of Click's medium containing 5% FCS at a cell density of $1 \times 10^6$ cells/ml in 24 well Nunc culture plate together with 100 μl of 5 μg/ml of phytohemmaglutinin-M(Gibco)(pHA), and cultured for 48 hrs under the conditions described above. The cells are washed and inoculated again in 1 ml of Click's medium at a cell density of $1 \times 10^5$ cells/ml together with 1 ml of a conditioned medium which has been prepared from human splenocytes stimulated by 2.5 μg/ml of concanavalin A (hereinafter "Con A") for 48 hrs, and the culture medium containing 50% conditioned medium is exchanged in every three days to get long term culture of human T lymphocytes from PBL. The thus prepared long term cultured human T lymphocytes are cloned by the limiting dilution method as described above, in the presence of human splenocytes derived conditioned medium and the cell clones are propagated similarly. Thereafter cloned human T lymphocytes are inoculated in 1 ml of RPMI 1640 at a cell density of $1 \times 10^6$ cells/ml in 24 well Nunc culture plate in the presence of 10 μg/ml of PHA and cultured for 24 hrs at 37° C. in 7.5% $CO_2$ incubator. The supernatants of the culture liquid are harvested, centrifuged, filtered through a 0.22μ millipore filter and assayed for IL-2 activity to specify the IL-2 producing human normal T lymphocytes clones.

(3) Acquisition of malignant cell line derived from human lymphocytes capable of producing IL-2 in the presence of mitogen.

Jurkat cell line or cloned cell lines such as Jurkat 111 obtained by the limiting dilution method described above are able to produce from 10 to 4,000 units/ml of IL-2 when cultured for 24 hours in a serum free synthetic medium described previously or in RPMI 1640 containing 1–2% mammalian serum in the presence of a mitogen such as 10 μg/ml Con A or 2.5 μg/ml PHA. These malignant human cell lines also produce IL-2 when cultured in the presence of zinc chloride, protein A or picibanil.

(4) Acquisition of cells capable of producing IL-2 in the co-presence of a mitogen and other co-stimulatory cells or co-stimulatory soluble factors.

Human malignant cell line Molt 4F and some cloned cell lines such as Jurkat J99, obtained according to the limiting dilution method, do not produce IL-2 even when cultured for 24 to 72 hours in the presence of lectins or mitogens in any concentration. However, these cells become able to produce IL-2 in significant amount (10–100 μ/ml) during culture period of 24 hours at 37° C., when cocultured with 5–10 μ/ml interleukin 1, one of monokines, or with 50% number of K562 or Raji cells.

The extraction of IL-2 mRNA from cells activated by the manner as mentioned above is carried out according to the conventional well known procedures, irrespective of the difference of cell sources. For instance, cells are partially or completely disrupted by addition of a detergent such as NP-40, SDS, Triton-X and deoxycholic acid or by mechanical homogenization or freezethawing. To prevent degradation of RNA by ribonuclease during extraction of mRNA, it is preferred to add RNase inhibitors such as heparin, polyvinylsulfate, bentonite, macaroid, diethylpyrocarbonate or vanadyl complex. IL-2 mRNA can be obtained from precipitated polysome in the IL-2 biosynthesis, the polysome fraction is precipitated with anti-IL-2 antibody the mRNA is then obtained by extracting with a detergent.

The poly A-containing mRNA can be fractionated or concentrated by any conventional manner, such as by affinity chromatography or batch absorption on oligo dT-cellulose, poly U-sepharose of sepharose 2 B, sucrose density gradient centrifugation or by agarose gel electrophresis.

The mRNA fractions are then assayed for IL-2 mRNA activity by testing biological activities of proteins translated from the mRNA fractions or by identifying the translated protein using monoclonal antibody against the IL-2 peptide. For instance mRNA is usually translated into the corresponding protein by microinjection into frog (*Xenopus laevis*) egg (Gurdon, J. B., et al., Nature, 233, 177–182 (1972)) or by employing the mRNA dependent reticulolysate or wheat germ translation cell free systems.

The activity of IL-2 may be ascertained by the microassay procedure principally discussed by Gillis et. al (Gillis. S., et al., J. Immunol., 120, 2027–2033 (1978)). The assay monitors the IL-2 dependent cellular proliferation of a cytotoxic T lymphocyte cell lines (hereinafter "CTLL") generated according to the methods described by Gillis et al., That is, $4 \times 10^3$ CTLL cells are inoculated into 100 µl of RPMl 1640 medium containing 2% FCS in 96 well flat-bottomed microplates together with 100 µl of the serially diluted translation products. After 20 hours incubation at 37° C. in 5% $CO_2$ incubator, cells are pulsed for 4 hours with 0.5 µCi of $^3$H-TdR, harvested onto glass fibre strips with the aid of an automated cell harvester and then the incorporated radioactivity is measured by liquid scintillation counting. By these assay procedures, the CTLL cells cultured in the presence of IL-2 were found to incorporate $^3$H-TdR in a dose dependent manner resulting in the definite calculation of the amount of IL-2 contained in test samples. of IL-2 possesses the activity to promote the proliferation of T lymphocytes, which enables the measurement of IL-2 activity using an index of T cell growth activity. That is, five CTLL cells are transferred into 100 µl of DMEM containing 2% FCS in 96 well flat-bottomed microplates together with 100 µl of the serially diluted translation products. After 72 to 96 hours incubation at 37° C. in a 5% $CO_2$ incubator, the number of cells grown and activated is counted under microscopy. As an positive external control group, 100 units/ml, 10 units/ml of IL-2 are added and the IL-2 activity of the test sample is calculated in comparison with the number of grown viable cells in these control groups.

The thus obtained IL-2 mRNA from the most active fraction is used as a template to synthesize ds-cDNA and the ds-cDNA is connected with a vector DNA.- Synthesis of cDNA is carried out by conventional procedures.

At first ss-cDNA which is complementary to mRNA is prepared in the presence of dATP, dGTP, dCTP, dTTP employing reverse transcriptase and using mRNA as a template and oligo-dT as a primer. The template mRNA is then removed by alkaline treatment and ds-cDNA is achieved by employing reverse transcriptase or DNA polymerase and using the above synthesized ss-cDNA as a template.

DNA produced recombinantly is prepared from the ds-cDNA thus obtained and a vector DNA containing replicon capable of replicating in eucaryotic or procaryotic cells. The recombinant DNA is thereafter incorporated into the host cells.

The ds-cDNA and a vector DNA capable of propagating in eucaryotic or procaryotic cells are, prior to ligation, modified by various procedures such as exonuclease treatment, addition of chemically synthesized DNA pieces and G, C-tailing to give ligatable termini to the ends of the ds-cDNA and the vector DNA. Ligation of the ligatable DNAs is performed by, for example, T4-phage DNA ligase in the presence of ATP.

With the recombinant DNA thus obtained, living cells are transformed to amplify the cloned cDNA or to produce IL-2 poly-peptide.

Suitable eucaryotic host organisms, which are usually used for production of IL-2, include vertebrates, yeasts and so on. For instance, monkey cells, e.g. CV-1 cells, transformed by an origin defective mutant of SV-40 and expressing the SV-40 large T antigen (COS cells) as discussed by Y. Gluzman (Cell, 23, 175–182, 1981), mouse derived cells discussed by Ohno, S and Taniguchi, T (Nucleic Acids Research, 10, 967–977, (1982)), and yeast host-vector systems applied for the expression of IFN gene, discussed by R. Hitzeman et al. (Nature, 293, 717–722,(1981)) may be used. Suitable procaryotic host organisms include *Escheyichia coli*, *Bacillus subtilis* and so on. For the amplification of DNA in host organisms, it may be preferred to use *E. coli* as a host, however other hosts can also be employed.

Suitable vectors used for *E. coli* include EK type plasmid vector (stringent type): pSC101, pRK353, pRK646, pRK248, pDF41 etc., EK type plasmid vector (relaxed type): ColE1, pVH51, pAC105, RSF2124, pCR1, pMB9, pBR313, pBR322, pBR324, pBR325, pBR327, pBR328, pKY2289, pKY2700, pKN80, pKC7, pKB158, pMK2004, pACYC1, pACYC184, dul etc. λ gt type phage vector: λgt. λc, λgr. λB, λWES, λC, λWES. λB, λZJvir., λB', λALO, λB, λWES. Ts622, λDam etc.. In general pBR322 has been frequently used as a vector for *E. coli* and in that instance the best cloning sites are the Pst I and EcoRI sites.

Transformation of the host cell with the recombinant DNA may be carried out by conventionally used manner as follows:

Where the host is Of procaryote such as *E. coli*, competent cells which are capable of DNA uptake are prepared from cells harvested after exponential growth phase and subsquently treated by the $CaCl_2$-method by well known procedures. When $MgCl_2$ of RbCl exists in the transformation reaction medium, the transformation efficiency increases. Transformation can be also performed after forming a protoplast of the host cell.

Where the host used is an eucaryote, transfection method of DNA as calcium phosphate-precipitates, conventional mechanical procedures such as microinjection, insertion of a plasmid encapsulated in red blood cell hosts or in liposomes, treatment of cells with agents such as lysophosphatidylcholine, or use of virus vectors, or the like may be used.

Cells possessing IL-2 gene can be isolated after the transformation, by either of the following two ways.

(1) In the plus-minus method, partially purified IL-2 mRNA is obtained by sucrose density gradient centrifugation of mRNAs extracted from mitogen activated mammalian cells as 11 to 12 s sediment and then 32 p-radiolabelled ss-cDNA is synthesized using the partially purified mRNA as a template. After removal of the template mRNA by alkaline treatment, isolated cDNA is hybridized with partially purified 11 to 12 s mRNA extracted from mitogen non activated mammalian cells. Thereafter nonhybridized and hybrid forming cDNA are fractionated on hydroxylapatite column chromatography. The non hybridized cDNA and hybridized cDNA are tentatively called probe A and probe B, respectively. Transformants are grown on two nitrocellulose filters in quite the same way: and the DNA of the cells is fixed on the filter paper by alkaline treatment. Probe A and Probe B are respectively hybridized with the DNA on two different filter papers and thereafter autoradiography assay is carried out to select the transformants which react positively to probe A (plus), but react weakly or do not at all to probe B (minus)(Taniguchi et al., Proc. Jpn. Acad., v 155B 464–469, 1979).

(2) The second method consists of dividing, for example, 1,000 to 10,000 transformant clones into several tens or several hundreds of clone groups. The divided clone groups are respectively cultured by conventional means to obtain plasmid DNAs. Thereafter these plasmid DNAs are converted into ss-cDNAs, for example, by heat denaturation, and the ss-cDNAs obtained are fixed onto nitrocellulose filter paper to achieve the hybridization of mRNA complementary to the fixed DNAs and prepared from mammalian cells including activated IL-2 mRNA. Alternatively, mRNAs containing IL-2 mRNA are hybridized with heat denatured plasmid DNAs and then DNA-mRNA hybrid is fixed onto nitrocellulose filter papers. These filter papers are then washed with low salt concentration buffer, such as 1 mM HEPES, or with 10 mM NaCl, and mRNA adsorbed on filter paper is extracted by treatment with a solution containing 0.5 mM EDTA and 0.1% SDS solution for e.g. 1 min. at 95° C. Purified mRNA is recovered by elution through oligo dT-cellulose column chromatography. Thereafter, the mRNA is translated into protein by microinjection into *Xenopus laevis* egg to ascertain IL-2 activity, or the mRNA is translated into a protein using the mRNA dependent reticulocyte or wheat germ in vitro cell free translation system, to analyse IL-2 activity using anti-IL-2 antibody. According to these procedures, the group in which the presence of IL-2 activity was detected was further divided repeatedly into groups consisting of smaller number of transformant clones until a single clone possessing IL-2 DNA is specified.

To obtain cDNA coding for IL-2 polypeptide from the IL-2 producing transformant, the recombinant DNA in the transformant is separated and cleaved with a restriction endonuclease. From the DNA fragments formed by the cleaving, the insert cDNA fraction is separated.

The complete nucleotide sequence of the PstI DNA insert coding for IL-2 polypeptides from the recombinant DNA of pIL2-50 A was determined by the procedure of Maxam and Gilbert (Meth. Enzym. 65. 499–560, (1980)) and by the dideoxynucleotide chain termination method (Smith, A. J. M. Meth. Enzym. 65, 560–580 (1980)).

Figure 5A:
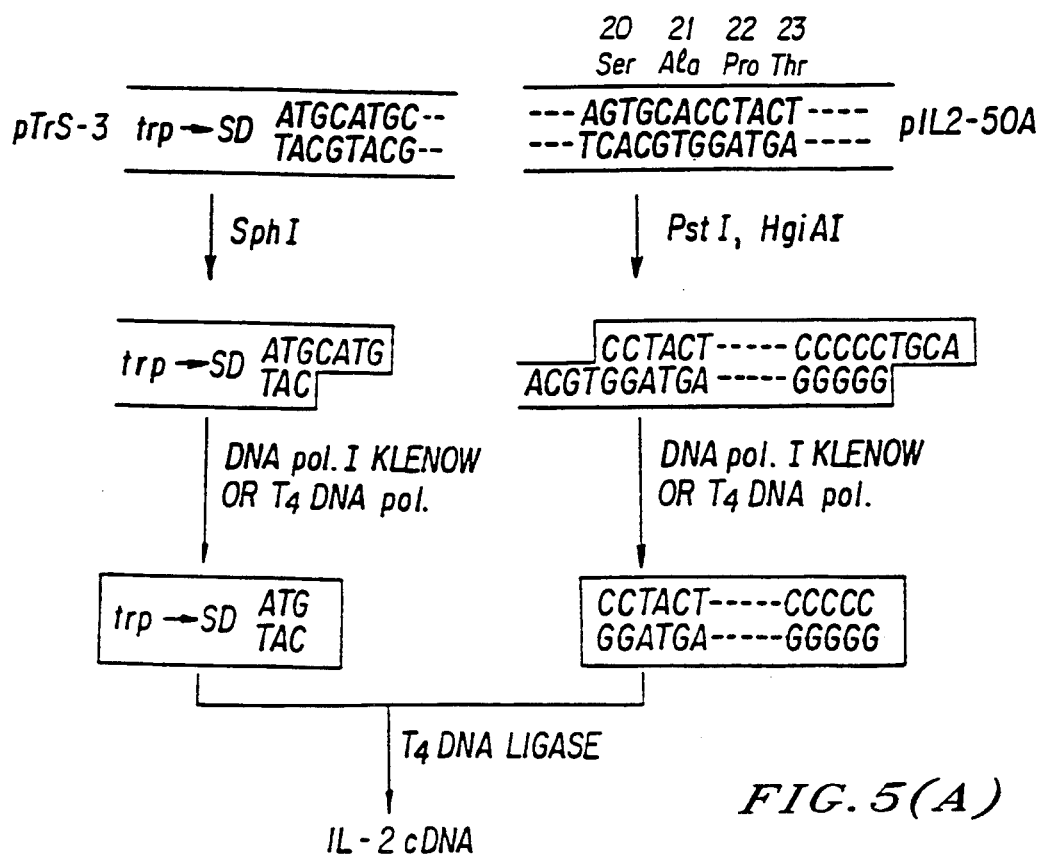
FIGS. 5(a), 5(b) and 5(c) are flow charts showing the construction of recombinant DNAs (pTIL 2-22, pTIL2-21, pTIL2-14 and pTIL2-15) using pTrS-3 as a vector. recombinant DNA (pKIL2-21) using pKT218 as a vector.
Figure 5A:
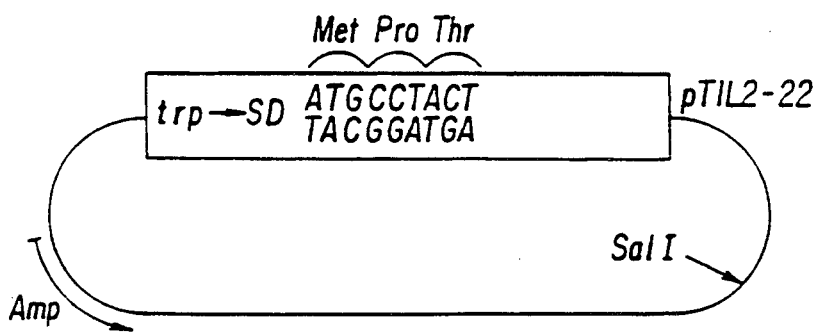
Figures 1, 5B:
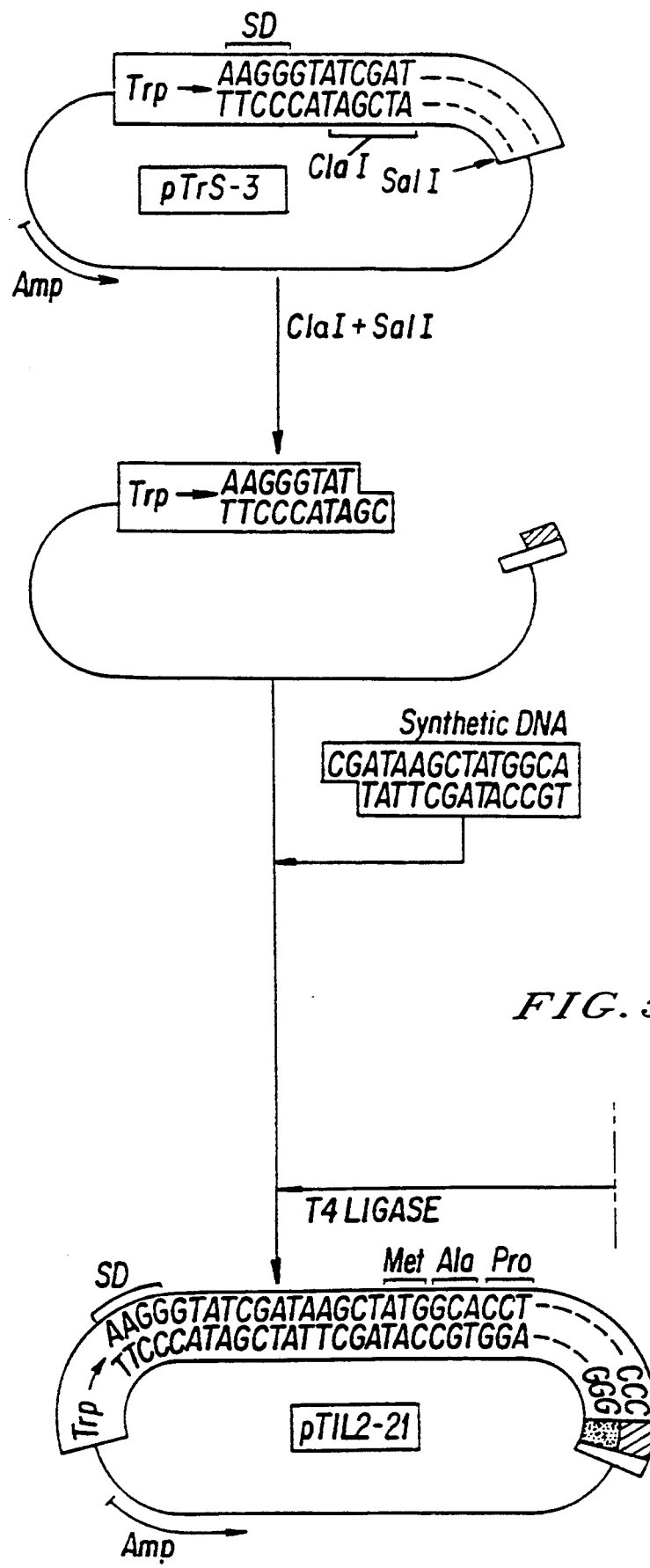
Figures 2, 5B:
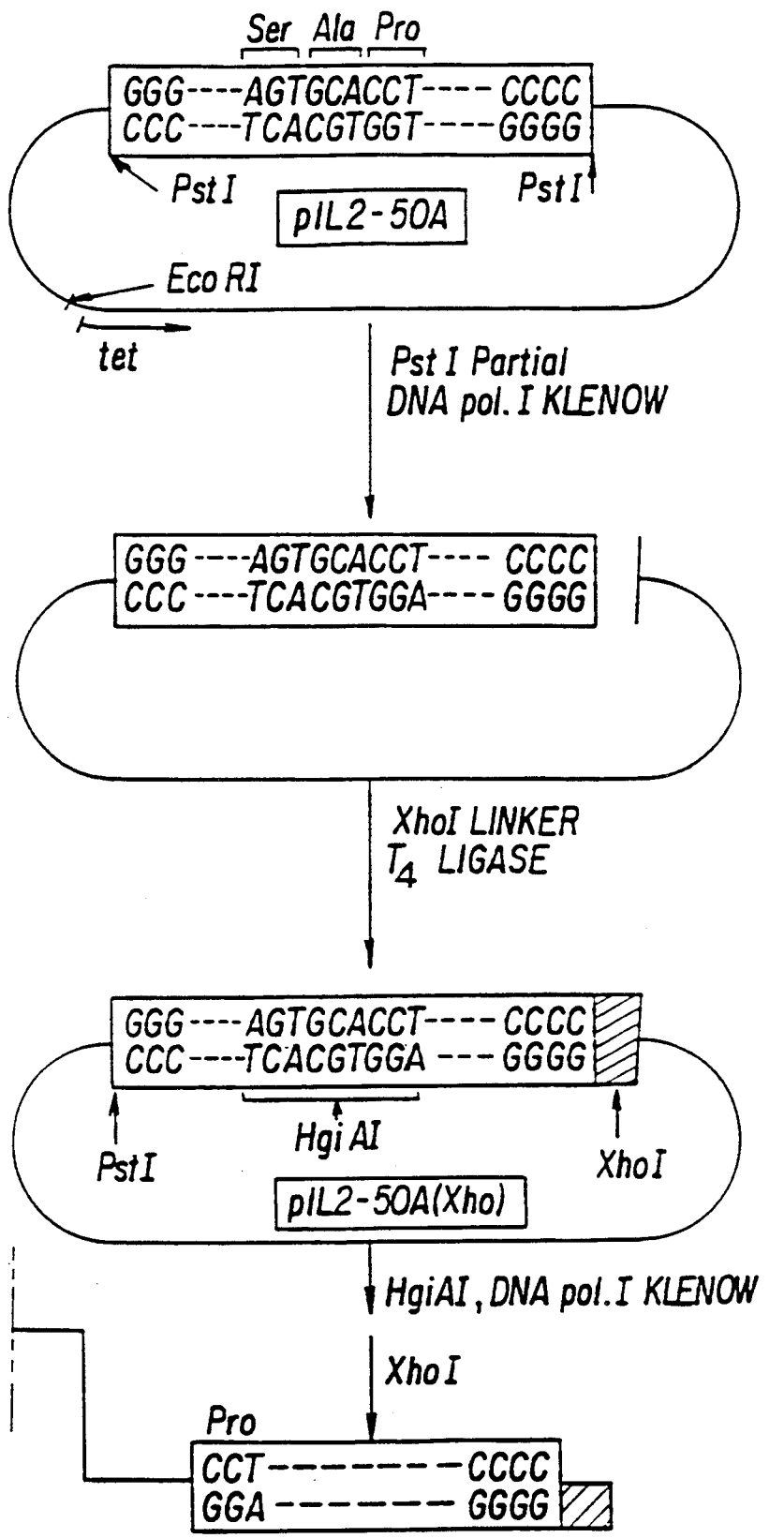
Figures 1, 5C:
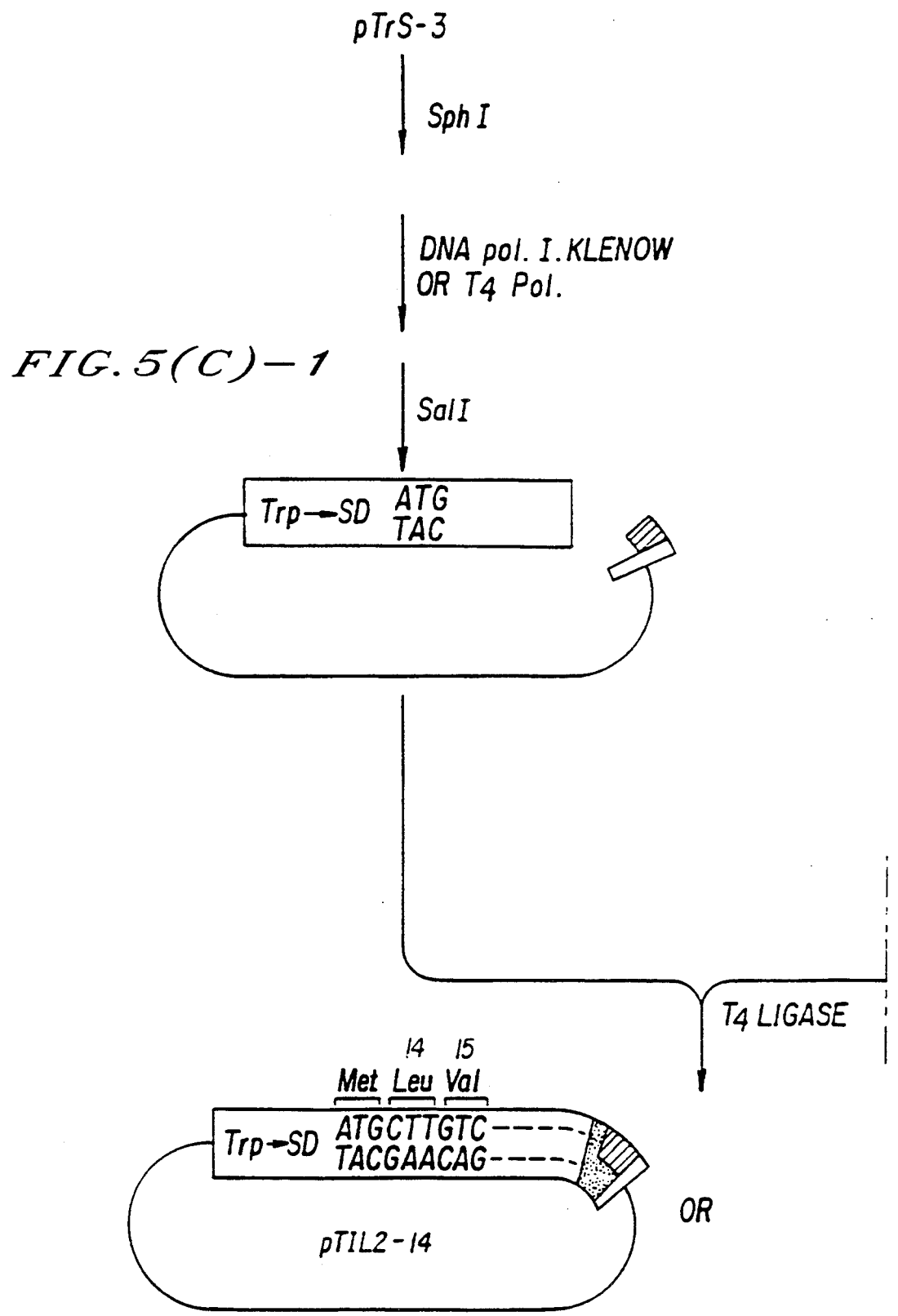
Figures 2, 5C:
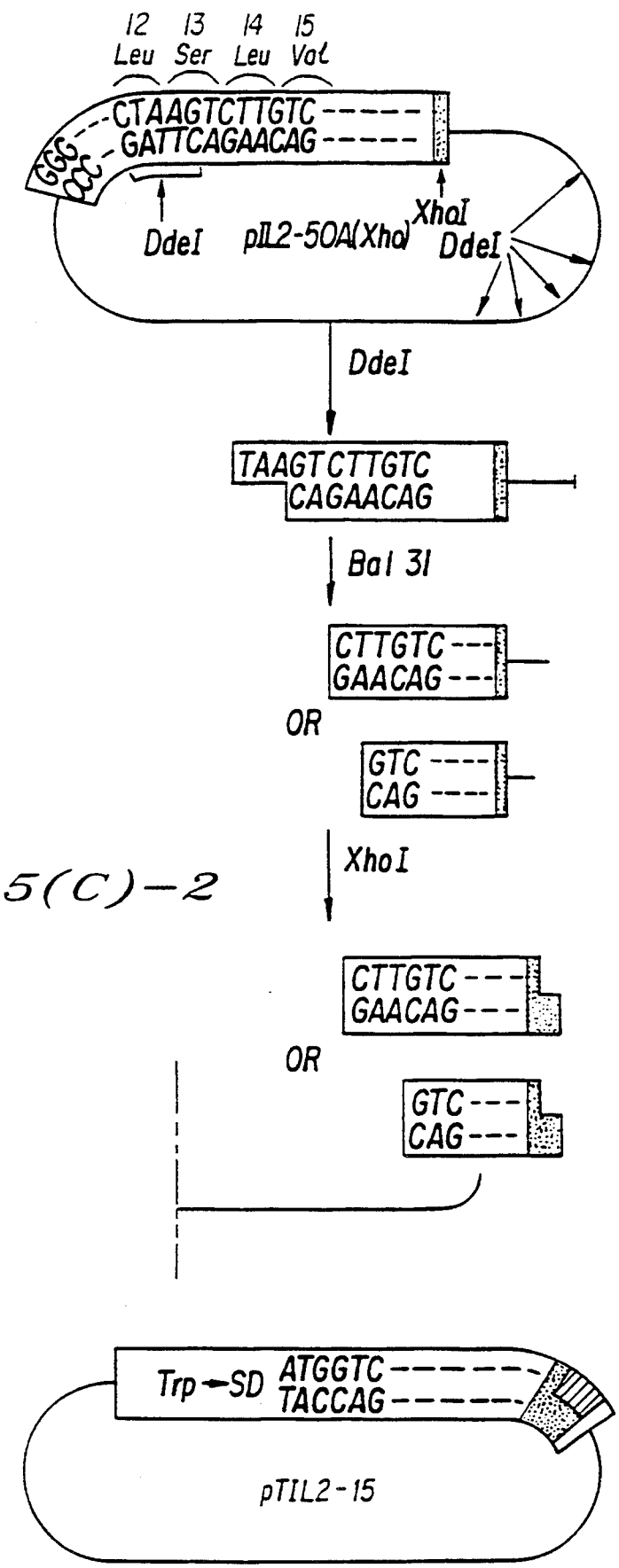

The restriction endonuclease cleavage map of the cDNA insert and base sequence of the insert are shown in FIG. 1, and FIG. 2(*a*) in which the cDNA has sites cleaved with restriction endonuclease of BstNI, XbaI and BstNI in this order, respectively.

The DNA Sequence of the insert contains a single large open reading frame. The first ATG sequence, which usually serves as the initiation sequence in eukaryotes (Kozak, M. Cell, 15, 1109–1123 (1978)), is found at nucleotides 48–50 from the 5' end. This ATG is followed by 152 codons before the termination triplet TGA is encountered at nucleotides 507 to 509.

A stretch of A residues corresponding to the 3'-poly (A) terminus of the mRNA is found at the end of the cDNA and this is preceeded by the hexanucleotide AATAAA (position 771–776) which is usually found in most eukaryotic mRNAs (Proudfoot, N. J. and Brownlee, C. G., Nature 263, 211–214, (1976)).

The amino acid sequence, for which the cDNA codes, could be deduced as shown in FIG. 2(*b*) (Amino Acid sequence I), and the polypeptide of the amino acid sequence I consists of 153 amino acids and its molecular weight is calculated to be 17631.7 daltons. As has been reported as a common feature in most of the secretion proteins known to date (Blobel, G. et al., Sym. Soc. exp. Med., 33, 9–36 (1979)), the N-terminal region of the deduced IL-2 polypeptide is also quite hydrophobic and this region probably serves as a signal peptide which is cleaved during the secretion process of the mature IL-2. Such cleavage occurs either between Ser and Ala at position 20 and 21 or between Ala and Pro at position 21 and 22 respectively, forming the polypeptide having amino acid sequences II and III, since similar cleavage sites have often been found in other secretion proteins (Blobel, G. et. al., Symp. Soc, exp. Med. 33, 9–36, (1979)). The mature IL-2 polypeptide would then contain 133 or 132 amino acids with the calculated molecular weight being 15420.5 daltons or 15349.4 daltons. This value is then compared with the reported value for human IL-2 protein from Jurkat cells (15,000 daltons) (Gillis, S et al., Immunological Rev , 63, 67–209, (1982)). Additionally, the DNA fragment initiating from CCT codon at position 111 to 113 in base sequence, which, therefore, codes for a polypeptide initiating from Pro at position 22 (Amino Acid Sequence III in FIG. 2(*b*)), was confirmed to express a polypeptide possessing IL-2 activity as shown in Example 5. It is also confirmed that the DNA fragment initiating from GCA sequence at position 107 to 110 in the base sequence, which therefore codes for a polypeptide initiating from Ala at position 21 (Amino Acid Sequence II in FIG. 2(*b*)) expresses a polypeptide possessing IL-2 activity as shown in Example 8.

It has been known that genes of eukaryotes often show polymorphism for example in human interferon genes. (Taniguchi et al. Gene 10. 11–15 (1980), Ohno & Taniguchi, Proc. Natl. Acad. Sci USA, 77, 5305–5309, (1986); Gray et al., Nature, 295 501–508 (1981)). In some cases, polymorphism is accompanied with replacement of certain amino acids of the protein products and in other cases, the structure of the protein product remains unchanged. In the case of human IL-2 cDNA, another cDNA clone (pIL2-503) in which the A residue at position 503 of DIL2-50A cDNA (FIG. 2) is replaced by a G residue can be detected. Other cDNA clones with some base substitution compared to pIL 2-50A cDNA can also be expected.

As can be understood from the above the genes of present invention include DNA having the base sequence shown in FIG. 2(*a*), DNAs initiating from ATG sequence at position 48 to 50 and having the sequential bases following the ATG sequence up to at least ACT sequence at position 504–506, DNAs initiating from GCA sequence at position 108–110 and having the sequential bases following the GCA sequence up to at least the ACT codon and DNAs initiating from CCT sequence at position 111-113 and having the sequencial bases following the CCT sequence up to at least the ACT sequence.

The genes of the present invention also include DNAs ending at the ACT sequence at position 504 to 506 and initiating from A at position 1, ATG sequence at position 48 to 50, GCA sequence at position 108 to 110 or CCT sequence at position 111 to 113. The genes of the present invention further include DNAs ending at TGA sequence at position 507 to 509 and initiating from A at position 1, ATG sequence at position 48 to 50, GCA sequence at position 108 to 110 or CCT sequence at position 111 to 113. The genes of the present invention further include DNAs ending at C at position 801 and initiating from A at position 1, ATG sequence at position 48 to 50, GCA sequence at position 108 to 110 or CCT sequence at position 111 to 113. The genes of the present invention additionally include DNAs ending with poly (A) and initiating from ATG codon at position 48–50, GCA sequence at position 108–110 or CCT sequence at position 111 to 113.

The genes of the present invention also include those of which base sequences correspond to Amino Acid Sequence I, II and III. Furthermore, polypeptides deficient in one or more amino acids in Amino Acid Sequence I, or polypeptides in which one or more amino acids in Amino Acid Sequence I are replaced with one or more amino acids may have IL-2 activity. Therefore genes coded for such polypeptides are suitable genes for the present invention. Similarly, genes having additive connection of one or more base sequences, capable of expressing one or more amino acids to Amino Acid Sequences I, II or III, are suitable in this invention so far as the additively connected amino acids do not interfere with the action of the polypeptides in expressing IL-2 activity. Modified additively connected amino acid region which interfere with the polypeptide function as IL-2, can be used in this invention so far as the additively connected region can be easily eliminated. This situation is quite the same for the additive connection of DNA to the 3'-terminus of genes corresponding to Amino Acid Sequence I, II and III coding additional amino acids at C-terminal of the I, II and III having Amino Acid Sequence I, II and III respectively. Therefore use of genes coded for such polypeptides are to be considered to be included in the present invention.

Recombinant DNAs which direct the production of IL-2 in living cells can be constructed by various methods. For example, the coding sequence of IL-2 cDNA can be inserted in an expression vechicle downstream of the promoter sequence. Alternatively, a cDNA piece carrying a promoter sequence can be inserted upstream of the IL-2 coding sequence, after or prior to, the insertion of cDNA in the expression vechcle.

Procedures to construct cells procariotic or eucaryotic which express the IL-2 cDNA and produce IL-2 polypeptide are. explained more precisely below:

(1) Expression of the IL-2 cDNA in *E. coli*

In order to express the IL-2 cDNA in *E. coli*, the cDNA is fused with various bacterial promoters and hybrid plasmids containing the cDNA downstream of the promoters are obtained. The plasmids are transfected into, for example *E. coli* HB101 strain and bacteria synthesizing a protein product with human IL-2 activity are cloned. Essentially any kind of bacterial promoter should direct the expression of IL-2 cDNA when they are abutted appropriately to the cDNA. Examples of this cDNA expression are described here.

The cloned cDNA for IL-2 encodes a polypeptide consisting of 153 amino acids as illustrated in FIG. 2. The N-terminal region corresponding to about 20 amino acids of this polypeptide is quite hydrophobic and this is characteristic of most of the secretion proteins. Such a hydrophobic sequence, so-called signal sequence, is cleaved during the secretion process. Therefore, mature IL-2 polypeptide should contain less than 153 amino acids. It is therefore desiable to express the cDNA portion encoding the mature IL-2 polypeptide but not the portion corresponding to the IL-2 signal sequence.

(i) Construction of an expression plasmid vechicle, pTrS-3, which includes *E. coli* trp promoter, its ribosome binding site (SD sequence) for the leader peptide was previously reported (G. Miozzari and Yanofsky, C. J. Bacteriol. 133, 1457–1466,(1978)) and an ATG codon situated 13 bp downstream of the SD sequence (Nishi et. al., SEIKAGAKU, 54, No. 8, 676 (1982)). The plasmid vehicle also contains a-single SphI site just downstream of the ATG intiation sequence (FIG. 4).

To express IL-2 cDNA, the plasmid is first digested by SphI and treated either with *E. coli* DNA polymerase I (Klenow Fragment) or with bacteriophage T4 DNA polymerase I to remove the 3' protruding ends (FIG. (a)). Plasmid pIL2-50A is double digested by PstI and HgiAI, and a larger cDNA fragment is isolated. The DNA is then treated either with *E. coli* DNA polymerase I (Klenow Fragment) or with bacteriophage T4 DNA polymerase so that the 3' protruding ends are rendered flush. The above treated cDNA encodes IL-2 polypeptide of 132 amino acids as shown in FIG. 5(*a*). This cDNA is then ligated to the pTrS-3 plasmid DNA pre-treated as above, such that the ATG initiation codon is abutted to the CCT (Pro) sequence of the IL-2 cDNA. Thus, a plasmid pTIL2-22 is obtained. The junction between trp promoter sequence and IL-2 cDNA sequence of pTIL2-22 is also illustrated in FIG. 5(*a*).

The plasmid pTIL2-22 should direct the synthesis in *E. coli* of an IL-2 polypeptide consisting 132 amino acids starting with proline.

Figure 4:
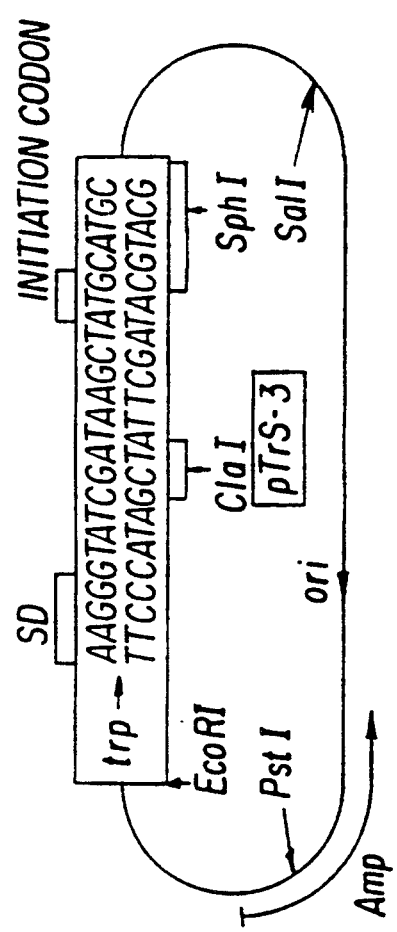
FIG. 4 shows the plasmid vector pTrS-3.

(ii) Since it is also possible that the mature IL-2 contains alanine (position 21) as the N-terminal amino acid instead of proline, the following plasmid which direct the synthesis of IL-2 polypeptide, consisting of 133 amino acids, is discussed, Plasmid pTrS-3 contains a single ClaI site between SD sequence and ATG sequence (FIG. 4). This plasmid is digested by Cla I and Sal I. Plasmid pIL2-50A is partially digested by PstI, treated with *E. coli* DNA polymerase I and the largest linear DNA is isolated. The DNA was then ligated with a synthetic DNA linker containing a restriction XhoII cleavage site and a clone containing the plasmid pIL2-50A (Xho) in which the linker DNA is introduced at the 3' downstream of IL-2 coding sequence is isolated. The plasmid pIL2-50A Xho) is first digested by HgiAI, treated either with *E. coli* Klenow Fragment or with T4 DNA plymerase, digested by XhoI and the cDNA fragment is isolated. This cDNA fragment is then ligated with pTrS-3 DNA pretreated with ClaI and SalI and with a synthetic DNA shown in FIG. 5(*b*). Thus, a plasmid pTIL2-21 which should direct the synthesis *E. coli* of an IL-2 polypeptide consisting 133 amino acids starting from alanine can be obtained as illustrated in FIG. 5(*b*). Similar construction can also be made without using XhoI linker.

(iii) IL-2 polypeptides with different size with different N-terminal amino acid can be produced by using the pTrS-3 expression plasmid vechicle by the following procedure. The cloned IL-2 cDNA in pIL2-50A contains a sole DdeI site at nucleotide position 81–85. Plasmid pIL2-50A(Xho) is digested by DdeI and the DNA fragment containing the larger portion of the cDNA is isolated. The fragment should also contain DNA of base about 3,0.00 pairs from pBR322 (FIG. 5(*c*)). The DNA fragment is treated by exonuclcease Bal 31 and then digested by XhoI. The above treated DNA is then ligated with pTrS-3 which is digested by SphI, treated either with Klenow Fragment or with T4 DNA polymerase and then digested by SalI as illustrated in FIG. 5(*c*). The ligated DNA is transfected into *E. coli* HB101 and bacterial clones expressing human IL-2 are screened. Those clones should express human IL-2 of various sizes since the DNA corresponding to the N-terminal region of human IL-2 is variably chewed away. Thus pTIL2-14 and pTIL2-15 carrying IL-2 cDNA could be obtained.

Figure 6:
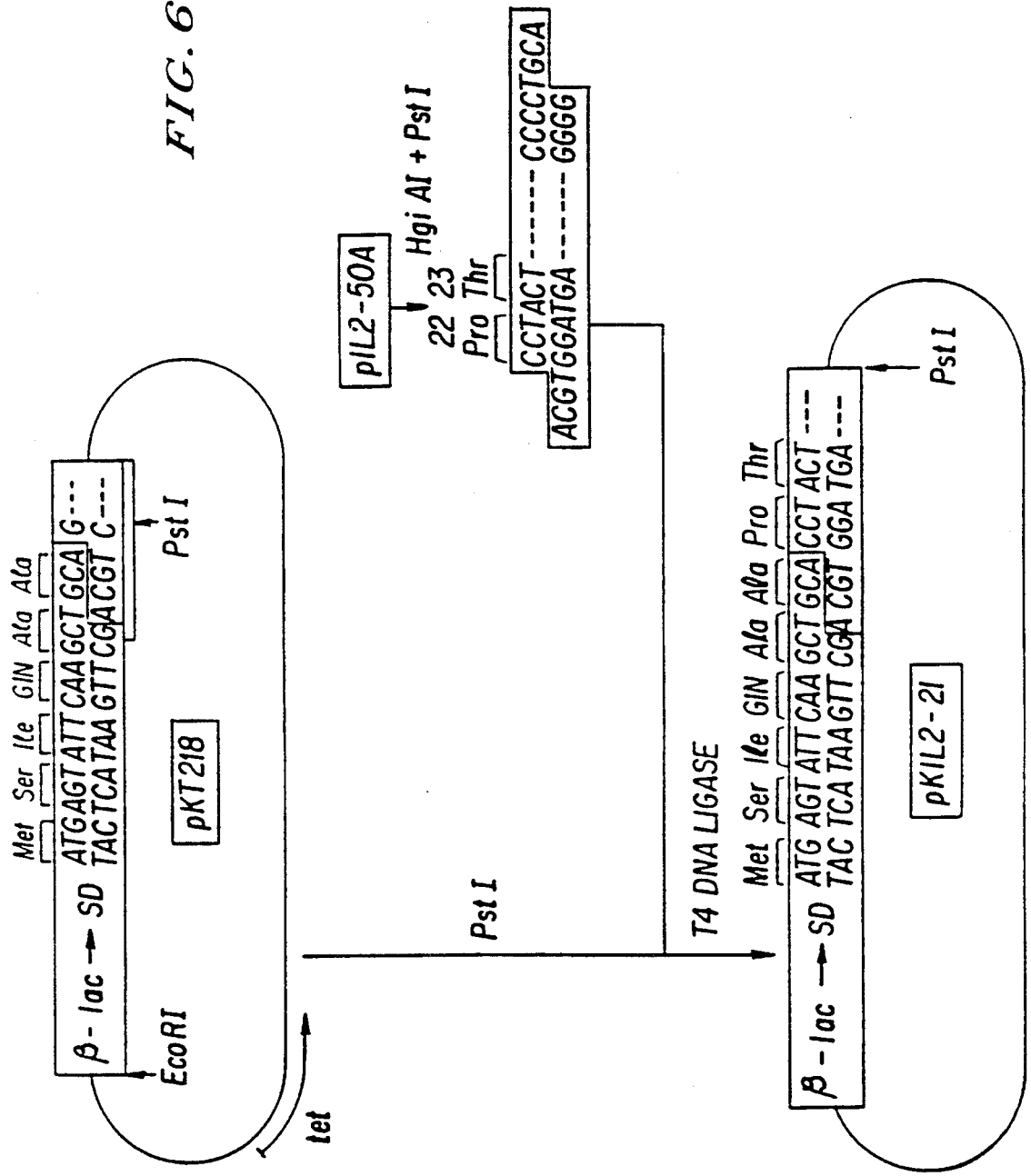
FIGS. 6 is a flow chart showing the construction of a FIG. 7 is a flow chart showing the construction of a recombinant DNA (pTuIL2-22) using pTUBlP-5 as a vector.

(iv) The IL-2 cDNA can also be expressed by the use of pKT218 (provided by K. Talmage)(Proc. Natl, Acad, Sci, USA, 77, p3369–3373, (1980)). Plasmid pKT218 is digested by Psti and ligated with an IL-2 cDNA insert obtained by digesting pIL2-50A DNA by HgiAI and PstI (FIG. 6). The resulting plasmid pKIL2-21 has the sequence at the beginning of the protein synthesis initiation as shown in FIG. 6. Thus, the plasmid pKIL2-21 should direct the synthesis in E. coli of a fused polypeptide consisting of 133 amino acids of IL-2 and amino acid of β-lactamase (The first methionine is cleaved off in E. coli).

Figure 7:
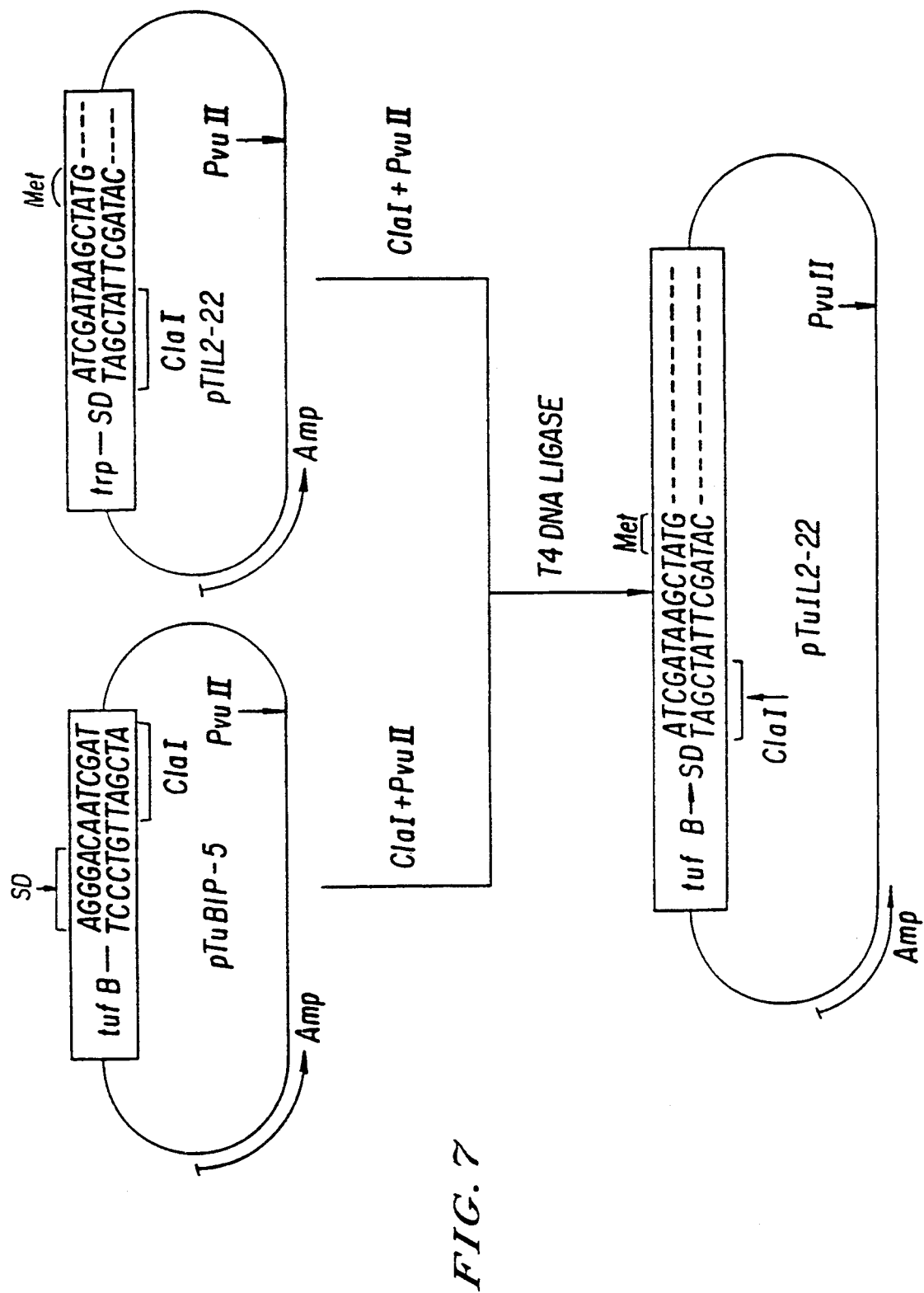

(v) An expression plasmid pTuBlP-5 in which the promoter sequence for tuf B is inserted into pBR322 was previously constructed (Taniguchi etal.-,SEIKAGAKU,53,966,(1981)). The plasmid contains a single ClaI site and this is located 2 bp downstream of the SD sequence as shown in FIG. 7.

Since pTrS-3 also contains a ClaI site between the SD sequence and ATG initiation sequence, and since this ClaI site is not destroyed during the construction of expression plasmid by using pTrS-3 and IL-2 cDNA as described above, it is very simple to replace the bacterial Trp promoter with that of tufB so that the human IL-2 cDNA is expressed under the control of tufB promoter. For example, pTIL2-22 is digested by ClaI and PvuII and the DNA fragment containing the IL-2 cDNA is isolated. This fragment is then ligated with pTUBIP-5 DNA, pre-digested by ClaI and PvuII and a plasmid pTuIL2-22 is constructed as illustrated in FIG. 7. The IL-2 activity could be detected in the extract of E. coli HB101 harboring the plasmid pTuIL2-22.

(vi) Similar construction can also be made by using, for example, pTIL2-21 and essentially all expression plasmids which are constructed with the use of pTrS-3. It is also possible to optimize the distance between SD and ATG sequence by digesting, for example, pTuIL2-22 with ClaI, removing (or adding) a few base pairs of DNA by Bal 31 or Sl or DNA polymerase I (E. coli) and then re-ligating the plasmid.

(2) Expression of the IL-2 cDNA in yeast

IL-2 cDNA can be also expressed in yeast by inserting the cDNA into appropriate expression vectors and introducing the product into the host cells. Various shuttle vectors for the expression of foreign genes in yeast have been reported (Heitzman. R. et al., Nature 293, 717–722 (1981); Valenzuela, P. et al., Nature 298, 347–350 (1982); Miyanoshita et al., Proc. Natl, Acad. Sci. USA 80, 1–5 (1983)). The vectors are capable of replicating both in E. coli and in yeast hosts and they contain promoter sequences of genes of yeast, essentially all such expression vectors can be used for the expression of IL-2 cDNA. It may be possible to achieve higher levels of IL-2 production by using yeast as compared to use of animal cells or bacteria. An example of human IL-2 cDNA expression in yeast is now described.

A yeast E. coli shuttle vectors pAT77 and pAM82 have been described by Miyanoshita et al. (Proc. Natl. Acad. Sci. USA 80, 1–5. (1983)). The vector pAM82 is a derivative of pAT77 and both carrying markers of ars 1 (Stinchcomb, D. T. et al, Nature 282, 39–43, (1979), 2 μm ori (Broach, J. R et al. Gene 8, 121–133 (1979)) and leu 2 (Ratzkin, B. et al. Proc. Natl. Acad. Sci. USA 74, 474–491 (1979)) and the promoter for the yeast acid phosphatase (APase) gene. They also carry a 3.7 kb DNA segment of pBR322 which contains an ampicillin resistance marker (Ap$^r$) and the origin of replication (FIG. 8). The APase promoter is inducible by shifting a high concentration of phosphate into a low concentration in the culture media. In order to express human IL-2 cDNA, pIL2-50A is digested by PstI after treating either by the E. coli Klenow Fragment of by T4 DNA polymerase, the cDNA is ligated with pAM82 previously digested by XhoI and incubated with the E. coli Klenow Fragment to fill in the ends. Hybrid plasmids in which the cDNA coding sequence are downstream of the yeast APase promoter sequence are selected by cloning them in E. coli. The obtained plasmid, pYIL-2a, is introduced into yeast and, after induction of the APase promoter, IL-2 activity in the yeast extract is measured. The plasmid pYIL-2a contains a stretch of GC residues between the yeast promoter and the IL-2 cDNA. It is possible that such a sequence inhibits the expression of IL-2 cDNA. In order to overcome this problem, following construction of a plasmid can be made: Plasmid pIL2-50A is digested by PstI and the cDNA insert is isolated. This cDNA is then treated by T4 DNA polymerase in the presence of dATP, dGTP and dTTP so that streches of C-residues at the both ends of the cDNA are chewed off and subsequently treated by Nuclease Sl, to remove stretches of G-residues. This DNA is ligated with XhoI DNA linker and plasmid pBR322 whose EcoRI site is cleaved and rendered flush by EcoRI and the Klenow Fragment, and the resulting plasmid, pIL2-Xho, is digested by XhoI and the cDNA insert is isolated. The cDNA is then introduced into the single XhoI site of pAM82 and a-plasmid containing the IL-2 coding sequence correctly. oriented with respect to the yeast APase promoter is cloned in E. coli. The plasmid, pYIL-2b, is introduced into yeast and, after induction of the APase promoter, IL-2 activity in the yeast extract is measured.

(3) Expression of the cDNA in mammalian cell

A plasmid which should direct the synthesis of human IL-2 in mammalian cells can be constructed as follows. A plasmid pCE-1 is constructed from pKCR (O'Hare, K., et al., Proc. Natl. Acad. Sci. USA., 78, 1527–1531, (1981)) and pBR328 (Soberon, X., et al., Gene, 9, 287–305, 1980) by a series of modification procedures as illustrated in FIG. 2, and initiation sequence ATG of IL-2 gene is connected to the downstream of the SV40 early gene. This plasmid contains a single PstI site just downstream of the SV40 early promoter and upstream of the part of the rabbit β-globin chromosomal gene containing one intron. The plasmid also contains the replication origin of SV40 as well as the polyadenylation site for the early gene. Thus a plasmid pCEIL-2, in which the IL-2 structural gene should be transcribed from the early promoter of SV40 in appropriate host cells, is obtained (FIG. 2).

This plasmid is digested by HhaI and then introduced by DNA transfection into the transformed monkey cell line COS-7 which allows replication of DNA containing SV40 origin sequences. It appears to be important to digest the plasmid by HhaI before transfection for the efficient expresssion of cDNA since sequences which could hamper replication of the transfected DNA in COS cells can be removed from the essential part of the plasmid for cDNA expression by this procedure. One to three days culture under conventional culture conditions after transfection of this vector to monkey cultured cell COS-7 (Gluzman, Y. Cell, vol. 23, 175–182, (1981)), IL-2 is usually secreted and produced in cultured cell medium. In order to insert amplified DNA into other eucaryotic cells, similarly a vector appropriate to host organisms is connected to cDNA insert cleaved and isolated from procaryotic cells and the eucaryotic cell may be transfected with thus synthesized vector and cultured.

Cells incorporating the recombinant DNA are cultured to amplify the recombinant DNA or to produce IL-2 polypeptide. The cultivation is carried out by conventional means. For instance, transformed yeast may be cultured in a medium containing source of carbon, a nitrogen source, inorganic salts and, when required, organic nutrients such as vitamin and amino acid at a temperature in the range from 20° to 37° C., and a pH ranging from 4 to 7 under aerobic condition. Transformed procaryotic organisms, such as *E. coli* or *B. subtilis* may also be cultured under conventional conditions.

The IL-2 produced intracellularly or extracellulary is recovered by any known method, such as precipition with ammonium sulfate, dialysis to remove salts (under normal or vacuum pressure), gel filtration, chromatography, preparative flat-bed iso-electric focusing, gel electropheresis, high performance liquid chromatography (hereinafter "HPLC"), (ion exchange, gel filtrtion and reverse phase chromatograqhy), and affinity chromatography on dye bound carrier, on activated Sepharose 4B (purified agarose) coupled with monoclonal antibody against said IL-2 or on lectin bound Sepharose 4B and the like. Methods of recovery, and purification of IL-2, are described in Watson et. al., J. Exp. Med., 150, 849–861 (1979), Gillis et. al., J. Immunol., 124, 1954–1962, (1980), Mochizuki et. al., J. Immunol Methods 39, 185–201, (1980), and Welte, K. et. al., J. Exp. Med., 156, 454–464 (1982).

The polypeptide thus obtained shows the same biochemical and biological behavior as has been known for IL-2 produced by mammalian cells by mitogen stimulation, and has IL-2 activity. The molecular weight is around 15,000 dalton and IL-2 activity was completely neutralized or precipitated with monoclonal anti-IL-2 antibody in the presence or absence of immunoadsorbents, such as Igsorb (Enzyme Center). In immunoelectrophoresis, the IL-2 polypeptide shows only a single precipitate against the corresponding anti-IL-2 antibody. The IL-2 activity remains stable after reduction with 2-mercaptoethanol, and is resistant to treatment with DNAse and RNAse as well as to heat treatment at 56° C. for 30 min.. The activity is stable at a pH between pH 2 to 9. The IL-2 produced could promote the growth of monoclonal functional T cells (cytotoxic T lymphocyte), enhance the thymocyte mitogenesis, give rise to the generation of anti-tumor specific cytotoxic T lymphocytes from memory state in the absence of the antigen, and could be used to augment natural killer cell activity against YAC-1 and RLô1 cells.

Having now generally described this invention, the same will become better understood by reference to certain specific examples which are included herein for purpose of illustration only and are not intended to be limiting unless otherwise specified.

EXAMPLE 1

(1) Human T leukemia cell line, Jurkat cells (freely available in Japan, W. Germany and United States) were suspended in RPMI 1640 medium containing 10 vol/vol % FCS and were irradiated with X-ray till 10,000 roentgen at a room temperature for 50 seconds using X-ray irradiation apparatus Exs 150/300-4 (Toshiba, Japan), and thereafter the irradiated cell was cultured for 5 days at 37° C. in 5% $CO_2$ incubator at a initial cell density of $1 \times 10^5$ cells/ml in the culture medium mentioned above. The mutated cells (0.2 cells/well) were placed in wells 10 pieces of flat-bottomed microplates having 96 wells, and cultured at 37° C. in 5% $CO_2$ incubator for 21 days.

Clones obtained from the wells showing growth were repeatedly transferred into fresh culture medium to propagate the clone sizes, and the propagated clones were cultured for 24 hrs at a initial cell density of $1 \times 10^6$ cells/ml in the presence of 50 μg/ml of Con A and IL-2 activity was measured according to the methods described before. Consequently a human T cell line designated as Jurkat-111 (hereinafter "J-111") (ATCC CRL8129), cloned from parent Jurkat, was selected, of which productivity of IL-2 was increased 40 times as much as that of the parent strain. The cloned cell line J-111 could grow under conventional conditions and the growth rate shows almost the same with ordinary Jurkat cells.

(2) Cells ($1 \times 10^5$/ml) of J-111 were inoculated in 1,000 ml of serum free synthetic culture medium RITC 55-9 (Sato, T. et al., Exp. Cell Res., 138, 127–134, (1982)) in roller culture bottles (Falcon 3027) and cultured for 4 days at 37° C., and cells propagated were harvested by centrifugation. The harvested cells were again inoculated in the medium mentioned above which had been added with 25 μg/ml of Con A to contain $4 \times 10^6$ cells/ml. In four batches of roller culture bottles (Falcon), 1,000 ml of the inoculated culture medium was placed into each batch. The cultivation was continued for 6 hours with rotating.

(3) Jurkat cells ($1.2 \times 10^6$) thus stimulated with 25 μg/ml of Con A for 6 hrs were suspended in 8,000 ml of phosphate buffer balanced with saline (hereinafter "PBS"). The cells were washed twice by centrifugation and were resuspended in 800 ml of RSB solution (10 mM Tris-HCl, pH 7.5, 10 mM NaCl, 1.5 mM $MgCl_2$) containing Ribonucleosides-Vanadyl Complex (10 mM), an inhibitor of nuclease. Then a detergent NP-40 was added to contain 0.05% as final concentration, followed by gentle mixing and the cell nuclei were removed by centrifugation for five minutes at 3,000 rpm at 4° C. SDS (0.5%) and EDTA (5 mM) were added to the supernatant and cytoplasmic RNA was extracted by addition of equal volume of phenol. After three times extraction with phenol, RNA was precipitated with two times volume of ethanol and precipitates were collected by centrifugation, which were solubilized in 10 mM Tris-HCl of pH 7.5. The amount of RNA obtained was 196 mg.

Fractionation of mRNA was carried out using affinity chromatography on oligo (dT) -Cellulose (P. L. Biochemicals, Type 7). An adsorption solution was a solution of pH 7.5 containing 20 mM Tris-HCl, 0.5M NaCl, 1 mM EDTA and 0.5% SDS and elution was carried out with water and 10 mM Tris-HCl1 (pH 7.5) by turns after washing the column with the buffer (20 mM Tris-HCl, pH 7.5, 0.5M NaCl, 1 mM EDTA) . The resultant mRNA eluted was 3.6 mg. Next, 2.4 mg of the mPNA obtained was fractionated by sucrose density gradient centrifugation (5 to 2.5% sucrose density gradient in a solution of pH 7.5 containing 50 mM Tris-HCl, 1 mM EDTA and 0.2M NaCl, centrifuged at 26,000 rpm for 24 hrs at 4° C., and 11 to 12 S fraction of mRNA was fractionated into fractions No. 12, 13, 14 in the amount of 59 μg, 46 μg and 60 μg, respectively.

(4) The mRNA obtained in fraction No. 13 was microinjected into the oocyte of *Xenopus laevis* (50 ng mRNA/egg) and the culture supernatant was served for the assay of IL-2 activity. As shown in Table 1, the increase of the incorporation of $^3$H-TdR and the increase of number of activated T lymphocytes were confirmed, clearly verifying that mRNA in this fraction contains human IL-2 mRNA.

TABLE 1

(a)

| Sample | Dilution | Uptake of $^3$H-TdR (cpm) | Amount of IL-2* (unit/ml) |
|---|---|---|---|
| Control I (Medium for assay) | — | 553 | 0 |
| Control II (Supernatant of egg culture non-treated) | × 2 | 590 | 0 |
|  | × 32 | 572 |  |
| Translation product of fraction 13 | × 8 | 14,683 | 32 |
|  | × 32 | 10,165 | . |

(b)

| | Dilution | Cell number of T-lymphocyte (No./well) | Amount of IL-2* (unit/ml) |
|---|---|---|---|
| Control I (Medium for assay) | × 2 | 0 | 0 |
|  | × 16 | 0 |  |
| Control II (Supernatant of egg culture non-treated) | × 2 | 0 | 0 |
|  | × 16 | 0 |  |
| Translation product of fraction 13 | × 2 | 115 | 40 |
|  | × 16 | 55 |  |

*The unit was calculated by comparing the amount of incorporated $^3$H-TdR with that of standard IL-2 (10 unit/ml) according to probit analysis.

(5) Thereafter cDNA was synthesized in vitro from No. 13 fraction of 11 to 12 S mRNA containing IL-2 mRNA and recombinant DNA was constructed with the plasmid vector PBR 322. With the recombinant DNA, *Escherichia coli* was transformed, and clone acquired IL-2 cDNA clones was selected, as follows:

(5-1) Fifty mM Tris-HCl buffer (pH 7.5), 30 mM NaCl, 6 mM MgCl$_2$, 5 mM dithiothreitol (hereinafter "DTT"), 0.5 mM of each dATP, dGTP, dCTP, dTTP (dCTP contained $^{32}$p radiolabelled one), 0.7 µg oligo (dT)$_{10}$, 10 µg mRNA and 15 unit AMV reverse transcriptidase (J. W. Beard) were mixed and maintained for 90 min. at 41° C.

After termination of the reaction, DNA was recovered as ethanol precipitates after the phenol treatment, and DNA was solubilized in a solution of pH 7.5 containing 20 mM Tris and 1 mM EDTA.

Two point five µg of ss-cDNA was synthesized. To remove mRNA present in this solution, the solution was made 0.33 N-NaOH by addition of NaOH, allowed to stand for 15 hrs at a room temperature, then the solution was neutralized with equal volume of 1 M-Tris-HCl of pH 7.5 and passed through "Sephadex G-50"(crosslinked dextrun) column. The recovered cDNA was 1.8 µg.

(5-2) Fifty mM phosphate buffer (pH 7.5), 10 mM MgCl$_2$, 10 mM DTT, 0.75 mM of each dATP, dGTP, dCTP, dTTP (dCTP contains $^3$H radiolabelled one), 1.8 µg ss-cDNA, and 8 unit of polymerase I (BRL, United States) were mixed and were allowed to react for 15 hrs at 15° C. After the termination of the reaction, DNA was recovered as ethanol precipitate, after treatments with phenol and with chloroform. 1.10 µg of ds-cDNA was generated. A mixture of 50 mM sodium acetate (pH 4.5), 0.2M NaCl, 1 mM ZnCl$_2$ and 1.10 µg of ds-cDNA was incubated for 20 min. at 37° C., added with 0.25 unit of nuclease S$_1$ (Sankyo, Japan), and incubated further for 15 min.

After the termination of the reaction, the reaction product treated twice with phenol was applied onto Sephadex G-50 to get 0.55 µg of ds-cDNA.

(5-3) A mixture of 0.14M potassium cacodylate, 30 mM Tris base, 0.1 mM DTT, 1 mM COCl$_2$, 0.64 mM 32P-dCTP (spc. act. 2.7×10$^6$ cpm/n mol), 0.55 µg of ds-cDNA and 5 unit of terminal transferase (BRL) were incubated for 7 min. at 37° C., then applied onto Sephadex G-50 column after phenol treatment to get 0.50 µg DNA as ethanol precipitates. The recovered DNA was found to be extended with around 50 dCMP residues at the both 3' terminus.

Ten µg of pBR 322 DNA was cleaved with restriction enzyme PstI, and 3'-termini of the cleaved DNA were added with dGMP chain, by the same method as that used in the addition of dCMP to ds-cDNA mentioned above, except dGTP was used in place of dCTP.

(5-4) A mixture of 50 mM Tris-HCl (pH 7.5), 0.1M NaCl, 5 mM EDTA, 0.05 µg of pBR 322 elongated with dGMP residues and 0.01 µg of cDNA extended with dCMP was incubated firstly for 2 min. at 65° C., then for 120 min. at 46° C., for 60 min. at 37° C. and finally for 60 min. at a room temperature. *E. coli*×1776 (Curtiss III, R. et al., in Molecular Cloning o Recombinant DNA, (W. A. Scott & R. Werner ed.) Academic Press, (1977)) was inoculated in 50 ml of L broth containing 100 µg/ml of diaminopimelic acid, 50 µg/ml of thymidine, 1% tryptophan, 0.5% yeast extract, 0.5% NaCl and 0.1% glucose and cultured in shaking at 37° C. until the absorbance of culture liquid at 562 nm became around O. D 0.3. After the termination of the culture, the culture liquid was left at 0° C. for 30 min., then the bacterial cells were collected by centrifugation followed by twice washing with 25 ml of a solution containing 5 mM Tris-HCl (pH 7.6), 0.1M NaCl, 5 mM MgCl$_2$ and 10 mM RbCl.

Thus obtained cells were suspended in 20 ml of a solution containing 5 mM Tris-HCl (pH 7.6), 0.25M KCl, 5 mM MgCl$_2$, 0.1M CaCl$_2$ and 10 mM RbCl and were left at 0° C. for 25 min., then cells were collected to resuspend them into 1 ml of the same solution, the recombinant DNA described above was added into 0.2 ml of the cell suspension and the suspension was left at 0° C. for 60 min. Then 0.7 ml of L broth was added to culture in shaking for 30 min. at 37° C. Thus obtained culture medium (0.1 ml) was thoroughly spread on the surface of 1.5% agarose medium composed of L broth containing 100 µg/ml diaminopimelic acid, 50 µg/ml thymidine and 15 µg/ml tetracycline, and incubated at 37° C. for two days.

(5-5) Four hundred and thirty two colonies appeared were divided into 18 groups, each containing 24 different bacterial clones, inoculated in 200 ml of L-broth containing 100 µg/ml of diaminopimelic acid, 50 µg/ml of thymidine and 10 µg/ml of tetracycline and cultured in shaking at 37° C. for 5 to 7 hrs. Then, 200 ml of fresh L-broth containing chloramphenicol at a final concentration of 170 µg/ml was added to culture further for an overnight. Thus amplified plasmid DNA was purified according to a conventional mean. Clones possessing IL-2 cDNA were screened by a mRNA hybridization-translation assay (hereinafter "H-T" assay"). H-T assay here employed was carried out as follows:

Purified DNA (25 µg) was cleaved with restriction enzyme Hind III, treated with phenol three times, treated with phenol-choroform and with chloroform, respectively, precipitated with ethanol, washed with 80% ethanol and dissolved in 40 µl of 80% formamide.

The reaction mixture was heated for denaturation at 90° C. for 5 min., then diluted to 1.3 ml with 10×SSC (1.5M NaCl, 0.15M sodium citrate). The DNA was thereafter fixed onto nitrocellulose filters, which filters were dried up at 80° C. for 3 hrs. and incubated for 18 hrs at 37° C. in the solution containing 50% formamide, 20 mM Pepes of pH 6.5, 0.75M NaCl, 5 mM EDTA, 0.2% SDS and 250 μg of poly (A) mRNA from induced J-111 cells to hybridize the DNA fixed on filters with IL-2 mRNA. Then the filters were washed at 65° C. three times with solution consisting of 10 mM Pipes of pH 6.5, 0.15M NaCl, 1 mM Pipes, 10 mM NaCl solution and treated with 0.5 mM EDTA, 0.1% SDS solution at 95° C. for 1 min. to recover the hybridized mRNA from the filters. Thus extracted mRNA was purified on oligo dT-Cellulose column according to the conventional methods and injected into Xenopus oocytes to determine the IL-2 activity of translated proteins. One out of 18 groups, each consisting of 24 clones, gave positive 48 unit/ml IL-2 activity in 3H-TdR incorporation assay described previously, while others being clearly negative. Then 24 single colonies belonging to the positive group were inoculated in 200 ml of L-broth possessing the same composition described, cultured aerobically for 5 to 7 hrs. at 37° C. and similarly chloramphenicol containing fresh L-broth was further added. After amplification of plasmid DNA by an overnight culture, plasmid DNA was similarly purified according to the standard procedures. After cleavage of about 5 μg of each plasmid DNA with Hind III, each plasmid DNA was bound to nitrocellulose filters similarly. The filters were hybridized with IL-2 mRNA and hybridized mRNA was recovered to inject into Xenopus oocyte to determine the IL-2 activity of translated proteins.

As shown in Table 2, only plasmid DNA purified from a single colony, designated as p3-16, gave the positive IL-2 activity. Therefore this clone was identified as the clone possessing IL-2 cDNA (E. coli×1776/p3-16 AJ 11995 (FERM-BP-225)). Thus plasmid DNA, p3-16, was confirmed to share exactly the DNA (Il-2 gene) capable of forming the specific hybrid with IL-2 mRNA.

TABLE 2

(a)

| Sample | Dilution | Uptake of $^3$H-TdR (cpm) | Amount of IL-2 (unit/ml) |
|---|---|---|---|
| Control I (Medium for assay) | — | 2,010 | 0 |
| Control II (Supernatant of culture liquid of non-treated egg) | × 2 | 2,120 | 0 |
|  | × 32 | 2,482 |  |
| Translation product of mRNA | × 2 | 20,453 | 58 |
|  | × 32 | 20,961 |  |

(b)

| Sample | Dilution | Cell number of T lymphocyte (cells/well) | Amount of IL-2 (unit/ml) |
|---|---|---|---|
| Control I (Medium for assay) | — | 0 | 0 |
| Control II (Supernatant of culture liquid of non-treated egg) | × 2 | 0 | 0 |
|  | × 32 |  |  |
| Translation product of mRNA* | × 2 | 88 | 32 |
|  | × 32 | 42 |  |

*mRNA hybridized with cDNA from plasmid p3-16.

The cDNA insert of plasmid p3-16 showed characteristics to be cleaved by restriction enzyme XbaI at a single site and by BstNI at two sites, (at upstream and downstream of XbaI cleavage site). However the plasmid p3-16 contained a cDNA insert consisting of about 650 base pairs, which apparently corresponds to a part of IL-2 mRNA of 11 to 12 S size.

Therefore another cDNA library were prepared according to the procedure of Land et al. (Land et al., Nucleic Acids Res., vol 9, p2551, (1981)) using IL-2 mRNA as a template. Single stranded cDNA (1.6 μg) was synthesized by using 4 μg of IL-2 mRNA elongated by dCMP residues, and ds-cDNA was synthesized by using oligo (dG)$_{12-18}$ F as the primer for DNA polymerase I (Klenow fragment). The cDNA (0.6 μg) longer than 680-base pair DNA size marker was obtained by a sucrose gradient centrifugation and inserted into the PstI site of pBR322 by the standard G-C tailing method. After transformation of E. coli×1776 by the recombinant DNA, approximately 2,000 colonies were screened by in situ hybridization method of Grunstein-Hogness with nick-translated p3-16 cDNA insert as the probe and the colony containing plasmid pIL 2-50A containing around 850 base pairs and the transformed clone (E. coli×1776/pIL 2-50A, AJ 11996 (FERM-BP-226)) were identified. A restriction endonuclease cleavage maps of the cDNA insert of pIL 2-50A are shown in FIG. 1.

To isolate a gene coding for IL-2 peptide from transformed E. coli×1776 pIL 2-50A, plasmid DNA was digested with restriction enzyme PstI after isolation of DNA region from the cells according to the conventional means. Thus produced smaller fragment among generated two DNA fragments was DNA gene coding for IL-2 peptide. The complete nucleotide sequence of the PstI insert from pIL 2-50A was determined by the procedure of Maxam and Gilbert (Maxam, A. W. et al., Enzym. 65, 499–560, 1980), and the whole structure is shown in FIG. 2.

EXAMPLE 2

Figure 3:
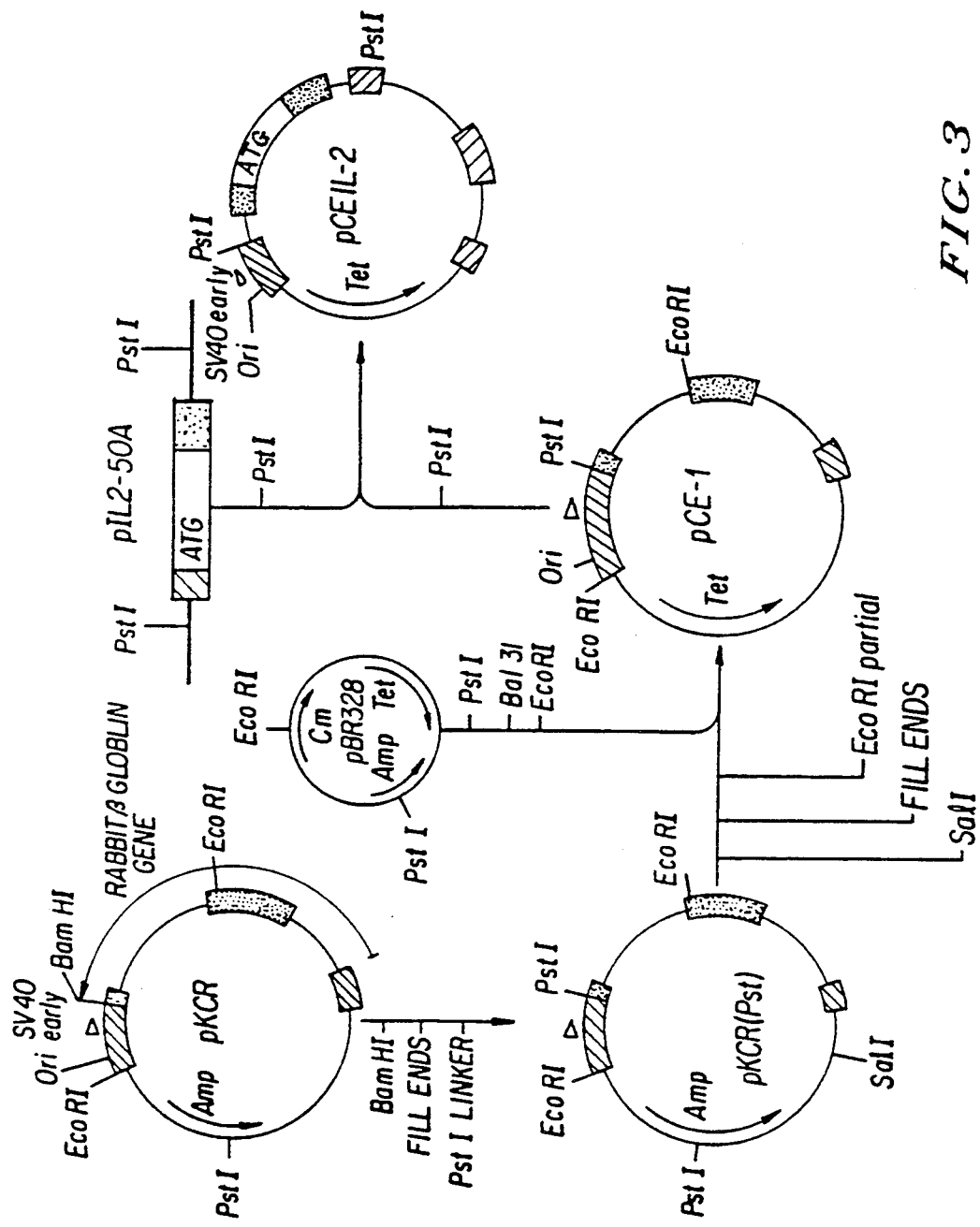
FIG. 3 is a flow chart showing the construction of a recombinant DNA (pCEIL-2), in which the coded gene is inserted.

The plasmid pKCR (O'Hare et al. Proc. Natl. Acad, Sci., USA, vol 78, No. 3, 1527–1531, (1981)) consists of (i) segments of SV40 DNA (shown as hatched blocks in FIG. 3) containing an early gene promoter and an origin of replication (0.725-0.648 m.u.) and a polyadenylation site from the early gene (0.169-0.144 m.u.) (ii) a part of the rabbit β-globin gene (shown as open blocks) (BamHI-PvuII fragment) (iii) a segment from pBR322 (EcoRI-BamHI fragment) containing an origin of replication and ampicillin resistance gene. This plasmid was cleaved by BamHI, and, after filling both ends of the cleaved DNA by DNA polymerase I (Klenow fragment), a synthetic PstI linker DNA was introduced to construct pKCR (PstI). Plasmid pKCR (PstI) was cleaved by SalI, treated by the Klenow fragment to fill the ends and then partially cleaved by EcoRI to obtain EcoRI-SalI fragment which contains the whole DNA derived from SV40 and the globin gene. This fragment was then ligated to a piece of pBR328 DNA which contains tetracycline resistance gene and an origin of replication as outlined in the FIG. 3. The resulting plasmid pCE-1 contains a single PstI site just downstream of the SV40 early promoter.

The cDNA insert of pIL 2-50A was excised by PstI cleavage and ligated to PstI-cleaved pCE-1 to construct pCEIL-2 in which expression of the IL-2 structural gene should be under control of SV40 early promoter. Plasmid pCE-1 was originally constructed for the cDNA cloning by G-C tailing method (Chang, A. C. Y. et al. Nature, 275, 617–624, 1978) in bacteria and direct expression in mammalian cells.

This plasmid was digested by HhaI and then introduced by DNA transfection (McCutchan et al., J. Natl. Cancer Inst. 41, 351–357, 1968) into the transformed monkey cell line COS-7 which allows replication of DNA containing SV40 origin sequences and is available from Gluzman, Y.(Cell, 23, 175–182, 1981). It appears to be important to digest the plasmid by HhaI before transfection for the efficient expression of cDNA since sequences which could hamper replication of the transfected DNA in COS cells can be removed from the essential part of the plasmid for cDNA expression by this procedure. COS-7 cells ($6 \times 10^4$/ml) were suspended in 0.5 mR of DMEM containing 5% FCS in 24 well culture plate (Nunc) and incubated for 4 hrs. at 37° C. Then mixture of 1 µg of the above described vector, 17.6 µl of 1 mM Tris-HCl containing 0.1 mM EDTA, 2.4 µl of 2M $CaCl_2$ and 120 µl of 2×HBS containing 50 mM Pipes, 280 mM NaCl, and 1.5 mM $Na_2HPO_4$.12-$H_2O$ (pH 7.10) were added to the cultured cells. The cells were further incubated for 4 hrs. at 37° C. and the culture medium was aspirated off, washed with 1 mR of PBS, then 0.5 ml of PBS containing 20% glycerol was added to leave at a room temperature for 3 min. Again the medium was aspirated off and the cells were washed with 1 ml of PBS and cultured in 1 ml of DMEM containing 5% FCS. Every 24 hrs., 500 µl of medium was exchanged with fresh medium. Each media, collected at appropriate interval was kept at 4° C. until use. Two to three days after the transfection, the cultured cell medium was assayed for the human IL-2 activity. As shown in Table 3 the resulting culture supernatant of COS-7 cell transfected with PCEIL-2 contained IL-2 activity. No IL-2 activity was detectable in the culture media of cells transfected with pCE-1.

TABLE 3

| DNA with which transfected | IL-2 activity measured by $^3$H-TdR uptake (µ/ml) | Growth of T-lymphocyte |
| --- | --- | --- |
| PCEIL-2 | 12 | ++++ |
| pCE-1 | 1 | − |

The IL-2 activity found in culture cell medium after transfection of COS-7 with pCEIL-2 was neutralized from 12 unit/ml to below 1 unit/ml by mouse (BALB/c) anti-human IL-2 monoclonal actibody. The result that COS-7 cell transfected with pCEIL-2 secreted human IL-2 clealy shows that cells of eukaryote transformed with a recombinant DNA comprising a gene coding for IL-2 polypeptide and a vector DNA capable of replicating in said cells can exactly useful for the production of IL-2.

The plasmid PCEIL-2 incorporated in *E. coli.* HB101 has been deposited in the accession number of FERM-BP 244.

EXAMPLE 3

*Escherichia coli*×1776/pIL 2-50A (AJ 11996 (FERM-BP-226)) prepared in Example 1 was inoculated in 250 ml of L broth, containing 100 µg/ml diaminopimelic acid, 50 µg/ml thymidine, 1% tryptophan, 0.5% yeast extracts, 0.5% NaCl and 0.1% glucose, and cultured with shaking at 37° C. till optical density at 562 nm of the cultured medium became 0.5. After the termination of the culture, cultured medium was allowed to stand at 0° C. for 30 min. and the cells were harvested by centrifugation, washed once with 20 mM Tris-HCl containing 30 mM NaCl and were resuspended in 1.8 ml of the same buffer. A solution containing 0.2 µl of lysozyme (10 mg/ml) and 20 µof 0.5M EDTA was then added to the cells and the mixture was allowed to stand at 0° C. for 20 min., followed by freeze-thawing three times successively. Then extracts of cells (1.5 ml) were obtained after centrifugation 40,000 rpm for 30 min. The extract was subjected to salting out with 85% ammonium sulfates, applied on Sephadex G15 to remove salts, then applied on DEAE cellulose column chromatography and the fraction eluted with 0.06M Tris-HCl buffer (pH 7.6) was pooled. Thus pooled fraction was freeze-dried and was applied on controlled pore glass beads (250Å, Funakoshi pharmaceuticals, Japan) chromatography to get IL-2 activity in eluant with 0.3M glycine-HCl buffer, where IL-2 containing fraction exerted 12 unit/ml of IL-2 activity. The results clearly indicate that *E. coli.*×1776/pIL 2-50A, AJ 11996 actually produces IL-2.

EXAMPLE 4

Constitutive IL-2 producer cell line J-A1886 (ATCC CRL8130), cloned from Jurkat cells according to the means described in Example 1, was similarly grown in roller culture bottle. The grown cells were resuspended in fresh synthetic medium RITC-55-9 at a initial cell density of $1 \times 10^6$ cells/ml and 8 hrs. after the start of the culture, the cells were served for the extraction of IL-2 mRNA as 11 to 12 S fraction, from $3 \times 10^9$ cells, according to the steps detailed in Example 1.

Double stranded cDNA was synthesized similarly as Example 1 and the cDNA longer than 600 base pairs (2.4 µg) was obtained after fractionation on a sucrose density gradient. The cDNA was then extended with dCMP residues using terminal deoxynucleotidyl transferase and an aliquot (50 ng) was annealed with 250 ng of dGMP-elongated, PstI-cleaved pBR322. The resulting hybrid plasmids were used to transform *E. coli.*×1776 and the transformants of around 4,000 clones were obtained. According to the Grunstein-Hogness method, three clones complementary with plasmid 3-16 cDNA used as a probe were selected. Namely thus selected clones are transformed clones possessing human IL-2 gene.

EXAMPLE 5

A plasmid which should direct the synthesis of human IL-2 in *E. coli.* cells was constructed as follows. A plasmid pTIL2-22 was constructed from pTrS-3 (Nishi T., Taniguchi T. et al., SEIKAGAKU 53,967, (1981)), and pIL 2-50A containing the IL-2 cDNA by a series of modification procedures as illustrated in FIG. 5(a). A plasmid pTrS-3 include insertion of the region of Trp promoter and Shine Dalgarno (hereinafter "SD") between EcoRI site and ClaI site of pBR322. The plasmid also contains an ATG initiation codon 13 bp downstream of the SD sequence as well as a single SphI site as illustrated in FIG. 4. The vector is very efficient to produce the said protein when DNA sequence corresponding to the said protein is inserted in phase just downstream of the ATG codon, which is generated by SphI digestion and by subsequent treatment by T4 DNA polymerase of pTrS-3. Therefore the plasmid pTrS-3 (30 µg) was cleaved with a restriction enzyme SphI in a conventional manner and after successive treatment with phenol and chloroform, ethanol precipitates were recovered, then both ends were rendered flush by the treatment of T4 DNA polymerase. Then the DNA (21.4 μg) was recovered by similar successive phenol, chloroform treatment and ethanol precipitation. On the other side, 380 μg of pIL 2-50A containing an IL-2 cDNA was cleaved by PstI and the IL-2 cDNA insert was isolated by agarose gel electrophoresis. cDNA insert (11 μg) was cleaved by HgiAI, treated by T4 DNA polymerase and 10 μg of the DNA of larger site was isolated by agarose gel electrophoresis. According to the procedures a cDNA (7.2 μg) coding for 132 amino acids was obtained and this DNA fragment had blunt ends (FIG. 5(a)). Then the thus obtained cDNA fragment ligated to a pTrS-3 vector, previously digested by SphI and treated by T4 DNA polymerase just downstream of ATG sequence. Thus ligated plasmid was then used to transform into *E. coli.* HB101 according to the conventional procedures. Ligation was carried out as follows. IL-2 cDNA (0.4 μg) larger fragment and 0.2 μg of pTrS-3 vector DNA were mixed with 0.8 unit of T4 DNA ligase in 66 mM Tris-HCl of pH 7.5 containing 6.6 mM MgCl$_2$, 1 mM ATP and 10 mM DTT, and the mixture was allowed to react at 4° C. overnight. Among the transformants appeared on L broth agar plate containing ampicillin, colonies containing the IL-2 cDNA portion, which encodes 132 amino acids were selected by in situ colony hybridization assay. Thus selected colonies were cultured (10 ml) again to prepare plasmid DNA by lysozyme treatment and by freeze-thawing. The plasmid DNAs were cleaved with PstI and XbaI, and the resulting products were analysed by agarose gel electrophoresis in order to identify pTIL 2-22 in which the cDNA was linked to the ATG sequence of pTrS-3 in correct orientation. The *E. coli.* HB101 containing pTIL 2-22 was a cultured under the conventional conditions known for the propagation of microorganisms. The cells were grown in 10 ml of X broth (2.5% Bactotrypton, 1.0% yeast extracts, 0.1% glucose, 20 mM MgSO$_4$, 50 mM Tris-HCl, pH 7.5) containing 25 μg/ml streptomycin and 25 μg of ampicillin at 37° C. for an overnight. One ml of the culture suspension was inoculated into the same X broth (100 ml) and cultured at 37° C. When O. D at 650 ml arrived around 1.5–2.0, 3-indole acrylic acid (IAA) was added. Three hours after the addition of inducer, the cells were collected, washed with 20 mM Tris-HCl (pH 7.5, 30 mM NaCl) and resuspended into 8 ml of the same buffer. For the efficient functioning of Trp promoter inducers such as IAA was added at a final concentration of 50 μg/ml. Thus produced proteins in bacterial cells were extracted by sonication (0° C. 2 min.) or lysozyme (8 μg) digestion (0° C., 20 min.) followed with three successive freeze-thawing. According to this procedures IL-2 was usually extracted from organisms. The extracted IL-2 activity ranged from 10,000 to 120,000 units/ml.

*E. coli.* HB101 containing pTIL 2-22 has been deposited in the accession number of FERM-BP 245.

EXAMPLE 6

A plasmid pTuIL 2-22, carrying IL-2 cDNA, was constructed from pTUBlP-5 (Taniguchi, T. et al., Seikagaku, 53, 966, 1981) and pTIL 2-22 shown in Example 5, by the procedures as illustrated in FIG. 7. A plasmid pTuBlP-5 includes insertion of the promoter sequence for tufB in PBR322. The plasmid also contains a single ClaI site and this is located 2 bP downstream of the SD sequence as shown in FIG. 7. Since pTrS-3 also contains a ClaI site between the SD sequence and ATG initiation codon, and since this ClaI site is not destroyed during the construction of expression plasmid by using pTrS-3 IL-2 cDNA as described in Example 5, it is very simple to replace the bacterial trp promoter with that of tufB so that the IL-2 cDNA is expressed under the control of tufB promoter.

Therefore the plasmid pTIL 2-22 (30 μg) was cleaved with a restriction enzyme ClaI and PvuII in a conventional manner. The fragment (ca 2.2 kb) containing IL-2 cDNA was isolated and purified by agarose gel electrophoresis to recover 3 μg of DNA. On the other side, 20 μg of pTuBIP-5 vector was cleaved similarly by ClaI and PvuII, and the larger fragment (ca. 3.4 kb) containing ampicillin resistant gene was isolated and purified by agarose gel electrophoresis to recover 3.5 μg of DNA. Then thus obtained two fragments, one (ca. 3.4 kb) containing tufB promoter, the other (ca. 2.2 kb) containing IL-2 cDNA, were ligated as follows. The fragment containing IL-2 cDNA (1.2 μg) and 0.3 μg of the fragment containing tufB promoter were mixed with 0.8 unit of T4 DNA ligase in 66 mM Tris-HCl of pH 7.5 containing 6.6 mM MgCl$_2$, 1 mM ATP and 10 mM DTT, and the mixture was allowed to react at 4° C. overnight. Thus ligated plasmid was then used to transform into *E. coli* HB101 according to the conventional procedures. Among the transformants appeared on L broth agar plate containing ampicillin, eight colonies containing the IL-2 cDNA portion such as pTuIL 2-22 in FIG. 7 were selected and plasmid DNA was prepared as described in Example 5. The *E. coli* HB101 containing pTuIL 2-22 were cultured in L broth (100 ml) at 37° C. When O. D at 650 mμ arrived around 0.5–1.0, the bacterial cells were collected, washed with 20 mM Tris-HCl (pH 7.5, 30 mM NaCl) and resuspended into 2 ml of the same buffer. Thus produced proteins were extracted similarly as Example 5. The extracted IL-2 activity ranged from 6,000 to 56,000 units/ml.

*Escherichia coli* HB101 containing pTuIL 2-22 has been deposited as in the accession number of FERM-BP 246.

EXAMPLE 7

A plasmid pGIL 2-22, carrying IL-2 cDNA was constructed from pGL 101 (Roberts, T. M. and Laucer G. D., Meth. Enzym., 68, 473–483, 1979) and FTIL 2-22 shown in Example 5.

The plasmid pGL 101 (20 μg) containing a lac promoter was cleaved with a restriction enzyme PvuII in a conventional manner to recover 17 μg of DNA by successive treatment with phenol, chloroform and ethanol precipitation. On the other side, pTIL 2-22 (75 μg) was cleaved with ClaI and SalI to recover 2.2 μg of a DNA fragment containing IL-2 cDNA by agarose gel electrophoresis. The fragment was rendered flush by the treatment with DNA polymerase I (Klenow fragment), then thus obtained two fragments (0.25 μg and 0.66 μg) were ligated with 1.0 unit of T4 DNA ligase in the same manner as Example 6. Thus ligated plasmid was then used to transform *E. coli* HB101 according to the conventional manner. Among the transformants, the transformants possessing the insertion of the ClaI-SalI fragment containing IL-2 cDNA as a probe. These transformants were then cultured in X broth (10 ml) containing 25 μg/ml of ampicillin and the plasmid DNA was prepared by the manner as described in Example 5. Thus the plasmid DNA possessing the initiation sequence ATG of IL-2 cDNA just downstream of a lac promoter was obtained by cleavage with PstI and XbaI.

Thus prepared pGIL 2-22 was inoculated in 100 ml of L-broth containing 25 µg/ml of ampicillin and 25 µg/ml of streptomycin and were cultured. When optical density at 650 mµ arrived around 0.5, isopropyl-β-D-thiogalactopyranoside (IPTG) was added in the concentration of 1 mM and one hour later the bacterial cells were collected and the cell extracts were prepared in the manner as described in Example 6. The extracted IL-2 activity ranged from 6,000 to 80,000 units/ml.

*Escherichia coli* HB101 containing pGIL 2-22 has been deposited in the accession number of FERM-BP 247.

EXAMPLE 8

Plasmid pTrS-3 (10 µg) was at first cleaved with the restriction enzyme SalI and the SalI site was rendered flush by the treatment with DNA polymerase (Klenow fragment) or with T4 DNA polymerase. After cleavage with ClaI, a larger fragment, containing the trp promoter region, was isolated by agarose gel electrophoresis in a conventional manner to recover 3 µg of DNA.

On the other side, 11 µg of cDNA insert obtained by the PstI cleavage of pIL2-50A was cleaved with HgiAI, treated with T4 DNA polymerase and a larger fragment was isolated and purified by agarose gel electrophoresis. Thus cDNA fragment coding for 132 amino acids of IL-2 was obtained in an amount of 7.2 µg. Then 0.45 µg of the fragment containing a trp promoter (described above), 0.5 µg of HgiAI-PstI fragment containing IL-2 cDNA and synthetic oligonucleotides (5=) CGA-TAAGC TATGGCA (3') ,and (3') TATT-CGATACCGT (5') (each 20 pmole) , both of which were phosphorylated at 5'-terminus, were ligated with 1 unit of T4 DNA ligase in the same manner as described in Example 5.

Thus ligated plasmid was then used to transform *E. coli* HB101. Among the transformants appeared, the target transformants were selected as follows. The candidate transformants able to hybridize with both of IL-2 cDNA and synthetic oligonucleotides were firstly selected by colony hybridization method, then the transformants possessing the insertion of DNA fragment initiating from CCT sequence at position III to 113 in FIG. 2(a) (CCTACT . . . ) just downstream of ATG GCA sequence were selected by PstI, XbaI cleavage.

The above transformant, which contains pTIL2-21*a* or pTIL2-21*b*, is cultured in L broth by the manner shown in Example 5, and high activities of IL-2 can be found in cell extracts of the transformants when assayed by the manner shown in Example 5.

*Escherichia coli* HB101 possessing pTIL2-21*a* (AJ 12013) and *Escherichia coli* HB101 possessing pTIL2-21*b* (AJ 12014) have been deposited in the assession numbers of FERM-BP 248 and FERM-BP 249 respectively.

The hosts, *E. coli*×*1776* and HB101 (Boyer H. W. et al., J. Mol. Biol. 41, 459, (1969)) used in the above Examples are known and available for any public. Additionally, the hosts can be obtained from the deposited transformants by culturing the transformants in L-broth at 37° C. to make release the respective recombinant DNAs in the transformants and separating strains which become sensitive to tetracycline and ampicillin as the hosts.

The plasmid vectors pBR322 (Which is commercially sold by, for example, Bethesda Research Laboratory), pCE-1, pTrS-3 and pGL101 are known and available for any public. In addition, the plasmid vectors can be obtained from the deposited transformants by separating the recombinant plasmid DNAs in the transformants by a conventional manner and by separating the plasmid vectors by the manners which are naturally obvious from the disclosures in the respective Examples. For example, pCE-1 can be obtained by digesting pCEIL-2 by PstI and separating larger DNA fragment formed. Additionally, pTrS-3 and pTuBIP-5 have been deposited as *E. coli* FERM-P 6735 and *E. coli* ATCC 31878 respectively.

Having now fully described this invention, it will be understood by those of skill in the art that the same can be performed within a wide and equivalent range of conditions, parameters and the like without affecting the spirit or scope of the invention or of any embodiment thereof.

What is claimed as new and desired to be secured by Letters Patent of the United States is:

1. An IL-2 polypeptide which is produced by culturing a recombinant microorganism containing a vector having inserted therein a cDNA encoding human interleukin-2, wherein said cDNA is derived from mRNA having a sedimentation coefficient of from 11 to 12 S and is isolated from a human lymphocyte derivative cell capable of producing IL-2, wherein said polypeptide has a biological activity of promotion of proliferation of cytotoxic T lymphocytes, has a molecular weight of about 15,000 daltons, is activity stable over a pH of 2–9, and exhibits a single precipitate when bound by anti-human-IL-2 antibody.

2. An IL-2 polypeptide which is produced by culturing a recombinant microorganism containing a microbial vector having inserted therein a cDNA having the following base sequence:

| GCA | CCT | ACT | TCA | AGT | TCT | ACA | AAG | AAA | ACA | CAG |
|-----|-----|-----|-----|-----|-----|-----|-----|-----|-----|-----|
| CTA | CAA | CTG | GAG | CAT | TTA | CTG | CTG | GAT | TTA | CAG |
| ATG | ATT | TTG | AAT | GGA | ATT | AAT | AAT | TAC | AAG | AAT |
| CCC | AAA | CTC | ACC | AGG | ATG | CTC | ACA | TTT | AAG | TTT |
| TAC | ATG | CCC | AAG | AAG | GCC | ACA | GAA | CTG | AAA | CAT |
| CTT | CAG | TGT | CTA | GAA | GAA | GAA | CTC | AAA | CCT | CTG |
| GAG | GAA | GTG | CTA | AAT | TTA | GCT | CAA | AGC | AAA | AAC |
| TTT | CAC | TTA | AGA | CCC | AGG | GAC | TTA | ATC | AGC | AAT |
| ATC | AAC | GTA | ATA | GTT | CTG | GAA | CTA | AAG | GGA | TCT |
| GAA | ACA | ACA | TTC | ATG | TGT | GAA | TAT | GCT | GAT | GAG |
| ACA | GCA | ACC | ATT | GTA | GAA | TTT | CTG | AAC | AGA | TGG |
| ATT | ACC | TTT | TGT | CAA | AGC | ATC | ATC | TCA | ACA | CTA |
| ACT. | | | | | | | | | | |

3. An IL-2 polypeptide which is produced by culturing a recombinant microorganism containing a microbial vector having inserted therein a cDNA having the following base sequence:

| GCA | CCT | ACT | TCA | AGT | TCT | ACA | AAG | AAA | ACA | CAG |
|-----|-----|-----|-----|-----|-----|-----|-----|-----|-----|-----|
| CTA | CAA | CTG | GAG | CAT | TTA | CTG | CTG | GAT | TTA | CAG |
| ATG | ATT | TTG | AAT | GGA | ATT | AAT | AAT | TAC | AAG | AAT |
| CCC | AAA | CTC | ACC | AGG | ATG | CTC | ACA | TTT | AAG | TTT |
| TAC | ATG | CCC | AAG | AAG | GCC | ACA | GAA | CTG | AAA | CAT |
| CTT | CAG | TGT | CTA | GAA | GAA | GAA | CTC | AAA | CCT | CTG |
| GAG | GAA | GTG | CTA | AAT | TTA | GCT | CAA | AGC | AAA | AAC |
| TTT | CAC | TTA | AGA | CCC | AGG | GAC | TTA | ATC | AGC | AAT |
| ATC | AAC | GTA | ATA | GTT | CTG | GAA | CTA | AAG | GGA | TCT |
| GAA | ACA | ACA | TTC | ATG | TGT | GAA | TAT | GCT | GAT | GAG |
| ACA | GCA | ACC | ATT | GTA | GAA | TTT | CTG | AAC | AGA | TGG |
| ATT | ACC | TTT | TGT | CAA | AGC | ATC | ATC | TCA | ACA | CTA |
| ACT. |     |     |     |     |     |     |     |     |     |     | harvesting said microorganism cells, obtaining extracts of said cells, and purifying said extracts by: salting out with ammonium sulfates, applying said extracts to Sephadex G-15 followed by elution, applying said extracts to DEAE cellulose column chromatography followed by elution, applying said extracts to controlled pore glass beads chromatography followed by elution, applying said extracts to a Sepharose column followed by elution, to yield an IL-2 polypeptide.

* * * * *

UNITED STATES PATENT AND TRADEMARK OFFICE
CERTIFICATE OF CORRECTION

PATENT NO. : 5,399,669
DATED : March 21, 1995
INVENTOR(S) : Tadatsugu TANIGUCHI, et al.

It is certified that error appears in the above-indentified patent and that said Letters Patent is hereby corrected as shown below:

On the title page, Item [75], the sixth inventor's name should read:

--Junji Hamuro--

Also on the title page, Item [54], and Column 1, Line 2, the title should read:

--RECOMBINANT IL-2 POLYPEPTIDES HAVING IL-2 ACTIVITY--

Signed and Sealed this

Thirteenth Day of June, 1995

*Attest:*

BRUCE LEHMAN

*Attesting Officer*     *Commissioner of Patents and Trademarks*